United States Patent
Bickerdike et al.

(10) Patent No.: US 8,791,117 B2
(45) Date of Patent: *Jul. 29, 2014

(54) CYCLIC GLYCYL-2-ALLYL PROLINE IMPROVES COGNITIVE PERFORMANCE IN IMPAIRED ANIMALS

(75) Inventors: Michael John Bickerdike, Auckland (NZ); Jian Guan, Waitakere (NZ)

(73) Assignee: Neuren Pharmaceuticals Limited, Auckland (NZ)

( * ) Notice: Subject to any disclaimer, the term of this patent is extended or adjusted under 35 U.S.C. 154(b) by 558 days.

This patent is subject to a terminal disclaimer.

(21) Appl. No.: 13/043,215

(22) Filed: Mar. 8, 2011

(65) Prior Publication Data

US 2011/0201614 A1 Aug. 18, 2011

Related U.S. Application Data

(63) Continuation-in-part of application No. 12/421,871, filed on Apr. 10, 2009, now abandoned, which is a continuation of application No. PCT/US2007/021744, filed on Oct. 10, 2007, application No. 13/043,215, which is a continuation-in-part of application No. 10/570,395, filed as application No. PCT/US2004/028308 on Aug. 31, 2004, now Pat. No. 8,067,425.

(60) Provisional application No. 60/851,106, filed on Oct. 11, 2006, provisional application No. 60/852,507, filed on Oct. 18, 2006, provisional application No. 60/499,956, filed on Sep. 3, 2003.

(51) Int. Cl.
| | |
|---|---|
| *A01N 43/58* | (2006.01) |
| *A01N 43/60* | (2006.01) |
| *A61K 31/50* | (2006.01) |
| *A61K 31/495* | (2006.01) |
| *C07D 241/36* | (2006.01) |
| *C07D 471/00* | (2006.01) |
| *C07D 487/00* | (2006.01) |
| *A61K 31/4985* | (2006.01) |
| *A61K 31/498* | (2006.01) |

(52) U.S. Cl.
CPC .......... *A61K 31/498* (2013.01); *A61K 31/4985* (2013.01)
USPC .......................................... 514/249; 544/349

(58) Field of Classification Search
CPC ... A61K 31/407; C07D 403/04; C07D 471/02
USPC .......................................... 514/249; 544/349
See application file for complete search history.

(56) References Cited

FOREIGN PATENT DOCUMENTS

WO    WO 99/40931    8/1999

OTHER PUBLICATIONS

Grossberg, Journal of Clinical Psychiatry, 2003, Wiley Interscience, vol. 64, suppl. 9, pp. 3-6.*
McMurray, Trends in Neuroscience, 2001, Elsevier Science, vol. 24, No. 11, pp. S32-S38.*
Shah et. al., Geriatrics, 2000, American Geriatrics Society, vol. 55, No. 9, pp. 62 and 65-68.*
Barber et. al., International Journal of Geriatric Psychiatry, 2001, John Wiley & Sons, vol. 16, pp. S12-S18.*
Office Action dated Dec. 21, 2010 in U.S. Appl. No. 10/570,395.
Reply to Office Action dated Oct. 12, 2010 in U.S. Appl. No. 10/570,395.
Office Action dated May 10, 2010 in U.S. Appl. No. 10/570,395.
Reply to Office Action dated Apr. 21, 2010 in U.S. Appl. No. 10/570,395.
Office Action dated Feb. 2, 2010 in U.S. Appl. No. 10/570,395.
Reply to Office Action dated Oct. 20, 2009 in U.S. Appl. No. 10/570,395.
Office Action dated May 28, 2009 in U.S. Appl. No. 10/570,395.
Office Action dated Jan. 21, 2010 in U.S. Appl. No. 10/570,395.
Reply to Office Action dated Mar. 13, 2009 in U.S. Appl. No. 10/570,395.
Office Action dated Feb. 2, 2009 in U.S. Appl. No. 10/570,395.
Second Preliminary Amendment dated Dec. 17, 2007 in U.S. Appl. No. 10/570,395.

* cited by examiner

*Primary Examiner* — Sarah Pihonak
(74) *Attorney, Agent, or Firm* — D. Benjamin Borson; Borson Law Group, PC

(57) ABSTRACT

Embodiments of this invention provide methods for therapeutic use of cyclic G-2-Allyl Proline to treat cognitive disorders as well as manufacture of medicaments including tablets, capsules, injectable solutions that are useful for treatment of such conditions.

22 Claims, 16 Drawing Sheets

CYCLIC GLYCYL-2-ALLYL PROLINE IMPROVES COGNITIVE PERFORMANCE IN IMPAIRED ANIMALS

CLAIM OF PRIORITY

This application is a Continuation-in-Part of U.S. Utility application Ser. No. 12/421,871, filed Apr. 10, 2009 entitled "Cyclic Glycyl-2-Allyl Proline Improves Cognitive Performance in Impaired Animals," Michael John Bickerdike and Jian Guan, inventors, which is a continuation of PCT/US2007/021744, filed Oct. 10, 2007, which claims priority to U.S. Provisional Patent Application No. 60/851,106, filed Oct. 11, 2006, entitled "Cyclic Glycyl-2-Allyl Proline Improves Cognitive Performance in Impaired Animals," Michael John Bickerdike and Jian Guan, inventors, and U.S. Provisional Patent Application No. 60/852,507, filed Oct. 18, 2008, entitled "Cyclic Glycyl-2-Allyl Proline Improves Cognitive Performance in Impaired Animals," Michael John Bickerdike and Jian Guan, inventors. This application is also a Continuation-in-Part of U.S. Utility application Ser. No. 10/570,395, filed Mar. 2, 2007, entitled 'Neuroprotective Bicyclic Compounds and Methods for Their Use,' Margaret Brimble, Jian Guan, and Frank Sieg, inventors, which is a 371(c)(1) National Phase Application of PCT/US04/28308, filed Aug. 31, 2004, which claims priority to U.S. Provisional Patent Application No. 60/499,956, filed Sep. 3, 2003. Each of the above applications is incorporated herein fully by reference.

FIELD OF THE INVENTION

The present invention relates to novel bicyclic compounds structurally related to diketopiperazines and methods for their therapeutic use. In particular, this invention relates to the neuroprotective activity of such compounds. More particularly, this invention relates to the use of cyclic Glycyl-2-Allyl Proline ("cyclic G-2-AllylP" or "cG-2-AllylP") and pharmaceutical compositions thereof in the treatment of cognitive disorders.

BACKGROUND

Cognitive disorders, i.e. impairments of memory and learning processes, have a significant detrimental effect on the quality of life of patients affected by it. Clinically recognized cognitive disorders vary from mild cognitive impairment through to dementias of varying severity.

Mild cognitive impairment ("MCI") is a transition stage between the cognitive changes of normal aging and the more serious problems caused by Alzheimer's disease. The amnestic subtype of MCI, which have been linked to development of Alzheimer's disease, significantly affects memory.

Dementia is a clinically recognised broad-spectrum syndrome consisting of degrees of loss of cognitive abilities. Dementia can be one of many symptoms of various neurological diseases or the main abnormality associated with the disease, as it is the case in Alzheimer's disease. (Adams and Victor's, Principle of Neurology, 7th ed.)

Most common causes of dementia include: cerebral atrophy associated with Alzheimer's disease, Lewy-bodies disease, frontotemporal lobar degeneration, Pick's disease; vascular narrowing or blockage in the brain (i.e. vascular dementia also known as multi-infarct dementia); Hunting-ton's disease, Parkinson's disease; head trauma; HIV infection or Down's syndrome.

Currently there only several medications that have been shown to afford at most a modest transient benefit to the patients. Cholinesterase inhibitors (anticholinesterases), such as donepezil (Aricept®), galantamine (Razadyne®, Razadyne ER®, Reminyl®, Nivalin®) and rivastigmine tartrate (Exelon®) have been show to be efficacious in mild to moderate Alzheimer's disease dementia. Exelon® has recently been approved for the treatment of mild to moderate dementia associated with Parkinson's disease. Memantine NMDA receptor antagonists are the first approved Alzheimer's disease medication acting on the glutamatergic system (Axura®, Akatinol®, Namenda®, Ebixa®). These drugs however have side effects which in some cases lead to discontinuation of the therapy.

With the increase in the life span and general aging of the population there is a need to develop drugs which could delay or alleviate the cognitive function in aging patients.

SUMMARY

We have previously shown in patent application PCT/US2004/02830 filed Aug. 31, 2004, expressly incorporated herein fully by reference, that cyclic GP analogues, including but not limited to cyclic cyclopentyl-G-2-MeP and cyclic-G-2-AllylP are neuroprotective and neuroregenerative. The inventors have now discovered that cyclic G-2-AllylP is effective in treatment of cognitive impairment.

Thus, one aspect of this invention provides novel cyclic compounds having the structural formulas and substituents described below.

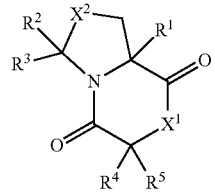

Formula 1

In some aspects, compounds of Formula 1 include substituents where:

$X^1$ is selected from the group consisting of NR', O and S;
$X^2$ is selected from the group consisting of $CH_2$, NR', O and S;
$R^1$, $R^2$, $R^3$, $R^4$ and $R^5$ are independently selected from the group consisting of —H, —OR', —SR', —NR'R', —$NO_2$, —CN, —C(O)R', —C(O)OR', —C(O)NR'R', —C(NR')NR'R', trihalomethyl, halogen, alkyl, substituted alkyl, heteroalkyl, substituted heteroalkyl, alkenyl, substituted alkenyl, alkynyl, substituted alkynyl, aryl, substituted aryl, heteroaryl, substituted heteroaryl, arylalkyl, substituted arylalkyl, heteroarylalkyl and substituted heteroarylalkyl; each R' is independently selected from the group consisting of —H, alkyl, heteroalkyl, alkenyl, alkynyl, aryl, arylalkyl, heteroaryl and heteroarylalkyl; or $R^4$ and $R^5$ taken together are —$CH_2$—$(CH_2)_n$—$CH_2$— where n is an integer from 0-6; or $R^2$ and $R^3$ taken together are —$CH_2$—$(CH_2)_n$—$CH_2$— where n is an integer from 0-6; with the proviso that when $R^1$=methyl and $R^2$=$R^3$=$R^4$=H then $R^5 \neq$benzyl and; when $R^1$=H, at least one of $R^2$ and $R^3 \neq$H.

In further aspects, this invention provides a compound of Formula 1 or a pharmaceutically acceptable salt, stereoisomer or hydrate thereof, wherein $R^1$=allyl, $R^2$=$R^3$=$R^4$=$R^5$=H, $X^1$=NH, $X^2$=$CH_2$ (cyclic Glycyl-2-AllylProline).

In still other aspects, this invention provides pharmaceutical compositions comprising a pharmaceutically acceptable excipient and a therapeutically effective amount of cyclic G-2AllylP.

In further aspects, this invention provides methods of treating an animal having a cognitive impairment, comprising administration to that animal an effective amount of a composition comprising cyclic G-2-AllylP. In yet further aspects, the animal to be treated is a human.

BRIEF DESCRIPTION OF THE DRAWINGS

This invention is described with reference to specific embodiments thereof. Other aspects of this invention can be appreciated with reference to the drawings, in which.

DETAILED DESCRIPTION

Definitions

Figure 1:
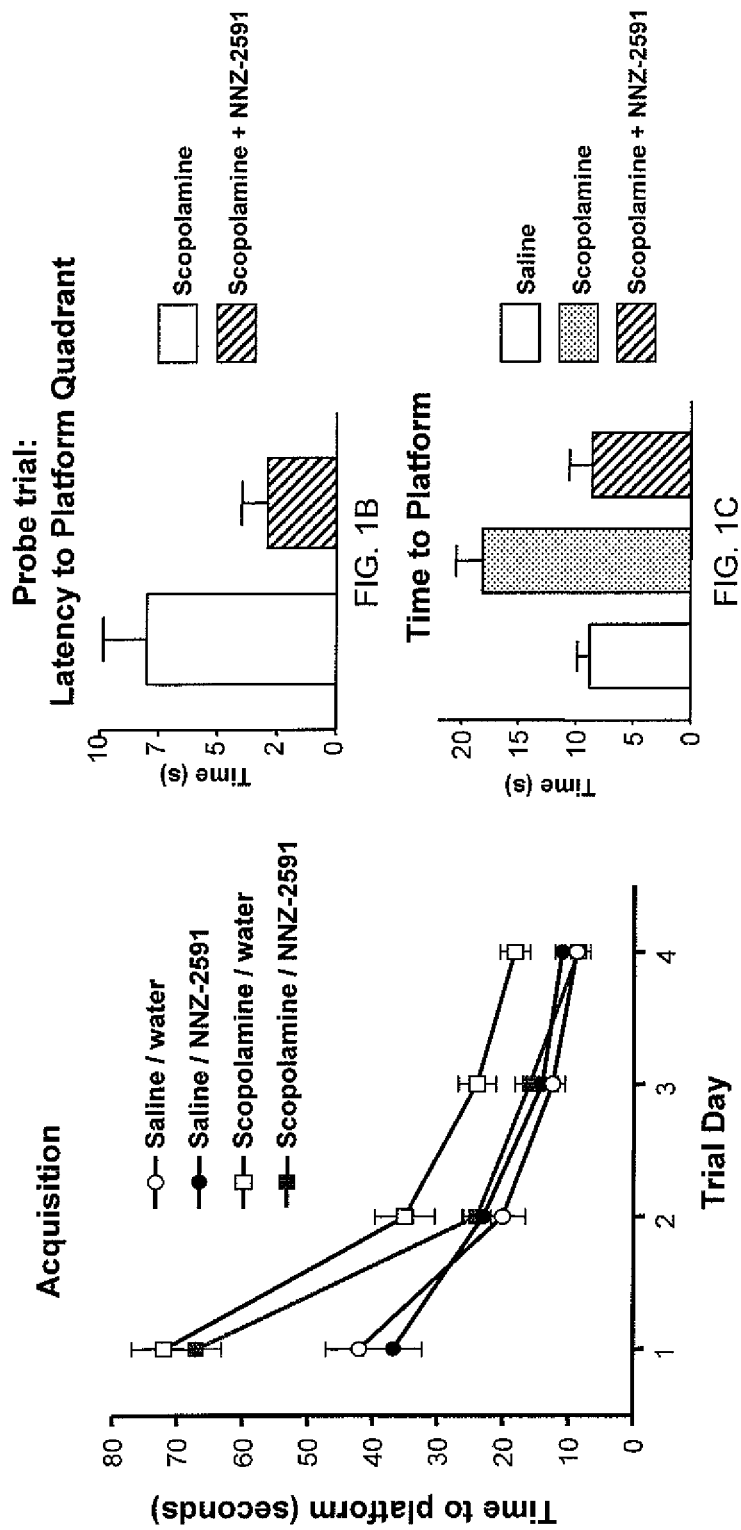
FIG. 1A is a graph showing effects of treatment with cyclic G-2-AllylP on the performance in acquisition phase (days 1-4) of the Morris Water Maze Test (MWMT) following scopolamine treatment.
FIG. 1B is a graph showing effects of treatment with cyclic G-2-AllylP on the latency to the platform quadrant in the probe test (day 5) of the MWMT.
FIG. 1C is a graph showing the time taken to find the platform on day $4^{th}$ of the acquisition phase for animals in 3 groups: (1) vehicle-treated, (2) scopolamine and cG-2AllylP-treated and (3) scopolamine—treated.

"Alkenyl" refers to an unsaturated branched, straight chain or cyclic hydrocarbon radical having at least one carbon-carbon double bond. The radical may be in either the cis or trans conformation about the double bond(s). Exemplary alkenyl groups include allyl, ethenyl, propenyl, isopropenyl, butenyl, isobutenyl, cyclopentenyl and the like. In some embodiments the alkenyl groups are $(C_2-C_6)$ alkenyl, and in other embodiments, allyl can be particularly useful.

"Alkyl" refers to a saturated branched, straight chain or cyclic hydrocarbon radical. Exemplary alkyl groups include methyl, ethyl, isopropyl, cyclopropyl, tert-butyl, cyclopropylmethyl, hexyl and the like. In some embodiments the alkyl groups are $(C_1-C_6)$ alkyl.

"Alkynyl", refers to an unsaturated branched, straight chain or cyclic hydrocarbon radical having at least one carbon-carbon triple bond. Exemplary alkynyl groups include ethynyl, propynyl, butynyl, isobutynyl and the like. In some embodiments the alkynyl group is $(C_2-C_6)$ alkynyl.

"Aryl" refers to an unsaturated cyclic hydrocarbon radical with a conjugated π electron system. Exemplary aryl groups include phenyl, naphthyl and the like. In some embodiments the aryl group is $(C_5-C_{20})$ aryl.

"Arylalkyl" refers to a straight chain alkyl, alkenyl or alkynyl group wherein one of the hydrogen atoms bound to the terminal carbon is replaced with an aryl group. Exemplary arylalkyl groups include benzyl, naphthylmethyl, benzylidene and the like.

"Cognitive Impairment" or "Cognitive Dysfunction" means one or more signs or symptoms of memory loss, loss of spatial orientation, decreased ability to learn, decreased ability to form short- or long-term memory, decreased episodic memory, decreased ability to consolidate memory, decreased spatial memory, decreased synaptogenesis, decreased synaptic stability, deficits in cognitive mapping and scene memory, deficits in declarative and relational memory, decreased rapid acquisition of configural or conjunctive associations, decreased context-specific encoding and retrieval of specific events, decreased episodic and/or episodic-like memory. Cognitive impairment can be observed in patients having Alzheimer's disease, Parkinson's disease, Lewy-bodies dementia and other disorders, as well in aging animals, including humans.

"Growth factor" refers to an extracellularly active polypeptide that stimulates a cell to grow or proliferate by interacting with a receptor on the cell.

"Heteroalkyl" refers to an alkyl moiety wherein one or more carbon atoms are replaced with another atom such as N, P, O, S etc. Exemplary heteroalkyl groups include pyrrolidine, morpholine, piperidine, piperazine, imidazolidine, pyrazolidine, tetrahydrofuran, $(C_1-C_{10})$ substituted amines, $(C_2-C_6)$ thioethers and the like.

"Heteroaryl" refers to an aryl moiety wherein one or more carbon atoms are replaced with another atom such as N, P, O, S etc. Exemplary heteroaryl groups include carbazole, furan, imidazole, indazole, indole, isoquinoline, purine, pyrazine, pyrazole, pyridazine, pyridine, pyrrole, thiazole, thiophene, triazole and the like.

"Injury" includes any acute or chronic damage of an animal that results in degeneration or death of cells in the nervous system. Such cells include neuronal cells and non-neuronal cells. Injury includes stroke, non-hemorrhagic stroke, traumatic brain injury, perinatal asphyxia associated with fetal distress such as following abruption, cord occlusion or associated with intrauterine growth retardation, perinatal asphyxia associated with failure of adequate resuscitation or respiration, severe CNS insults associated with near miss drowning, near miss cot death, carbon monoxide inhalation, ammonia or other gaseous intoxication, cardiac arrest, coma, meningitis, hypoglycemia and status epilepticus, episodes of cerebral asphyxia associated with coronary bypass surgery, hypotensive episodes and hypertensive crises, and cerebral trauma. It is to be understood that the above examples are by way of illustration only, and are not intended to be a complete listing of injuries capable of being treated by the compounds and methods of this invention.

A "pharmaceutically acceptable excipient" refers to an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

A "pharmaceutically acceptable salt" refers to a salt that is pharmaceutically acceptable and has the desired pharmacological properties. Such salts include salts that may be formed where acidic protons present in the compounds are capable of reacting with inorganic or organic bases. Suitable inorganic salts include those formed with the alkali metals, e.g. sodium and potassium, magnesium, calcium, and aluminium. Suitable organic salts include those formed with organic bases such as the amine bases e.g. ethanolamine, diethanolamine, triethanolamine, tromethamine, N-methylglucamine, and the like. Such salts also include acid addition salts formed with inorganic acids (e.g. hydrochloric and hydrobromic acids) and organic acids (e.g. acetic acid, citric acid, maleic acid, and the alkane- and arene-sulfonic acids such as methanesulfonic acid and benzenesulfonic acid). When there are two acidic groups present, a pharmaceutically acceptable salt may be a mono-acid mono-salt or a di-acid salt; and similarly where there are more than two acidic groups present, some or all of such groups can be present as salts.

A "protecting group" has the meaning conventionally associated with it in organic synthesis, i.e. a group that selectively blocks one or more reactive sites in a multifunctional compound such that a chemical reaction can be carried out selectively on another unprotected reactive site and such that the group can readily be removed after the selective reaction is complete.

A "stereoisomer" is a molecule having the structure of cyclic G-2-Allyl Praline, but having a chiral center. The term "cyclic G-2-Allyl Proline" includes all stereoisomers.

"Substituted" refers to where one or more of the hydrogen atoms on an alkyl, heteroalkyl, alkenyl, alkynyl, aryl, heteroaryl or arylalkyl radical are independently replaced with another substituent. Substituents include —R', —OR', —SR', —NR'R', —NO$_2$, —CN, —C(O)R', —C(O)OR', —C(O)NR'R', —C(NR')NR'R', —NR'—C(NR')—OR', —NR'—C(NR')—SR', NR'—C(NR')—NR'R', trihalomethyl and halogen where each R' is independently —H, alkyl, heteroalkyl, alkenyl, alkynyl, aryl, arylalkyl, heteroaryl or heteroarylalkyl.

A "therapeutically effective amount" means the amount that, when administered to an animal for treating a disease, is sufficient to effect treatment for a disease or an injury. A "therapeutically effective amount" means an amount that decreases adverse symptoms or findings, promotes desirable symptoms or findings, and/or treats an underlying disorder, and/or is curative.

"Treating" or "treatment" of a disease includes preventing the disease from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease).

Implicit hydrogen atoms (such as the hydrogens on the pyrrole ring, etc.) are omitted from the formulae for clarity, but should be understood to be present.

Compounds of the Invention

Certain embodiments of this invention include novel derivatives of cPG having structures as described below.

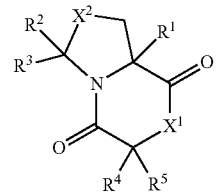

Formula 1

In certain embodiments, compounds of Formula 1 include substituents where:

$X^1$ is selected from the group consisting of NR', O and S;
$X^2$ is selected from the group consisting of CH$_2$, NR', O and S;
$R^1$, $R^2$, $R^3$, $R^4$ and $R^5$ are independently selected from the group consisting of —H, —OR', —SR', —NR'R', —NO$_2$, —CN, —C(O)R', —C(O)OR', —C(O)NR'R', —C(NR')NR'R', trihalomethyl, halogen, alkyl, substituted alkyl, heteroalkyl, substituted heteroalkyl, alkenyl, substituted alkenyl, alkynyl, substituted alkynyl, aryl, substituted aryl, heteroaryl, substituted heteroaryl, arylalkyl, substituted arylalkyl, heteroarylalkyl and substituted heteroarylalkyl; each R' is independently selected from the group consisting of —H, alkyl, heteroalkyl, alkenyl, alkynyl, aryl, arylalkyl, heteroaryl and heteroarylalkyl;

or $R^4$ and $R^5$ taken together are —CH$_2$—(CH$_2$)$_n$—CH$_2$— where n is an integer from 0-6;

or $R^2$ and $R^3$ taken together are —CH$_2$—(CH$_2$)$_n$—CH$_2$— where n is an integer from 0-6; with the proviso that when $R^1$=methyl and $R^2$=$R^3$=$R^4$=H then $R^5$≠benzyl and; when $R^1$=H, at least one of $R^2$ and $R^3$≠H.

In further embodiments, compounds of Formula 1 include substituents where:
$R^1$=methyl, $R^2$=$R^3$=$R^4$, $R^5$=H, $X^1$=NH, $X^2$=CH$_2$;
$R_1$=allyl, $R^2$=$R^3$=$R^4$=$R^5$=H, $X^1$=NH, $X^2$=CH$_2$;
$R^1$=$R^2$=$R^3$=H, $R^4$=$R^5$=methyl, $X^1$=NH, $X^2$=CH$_2$;
$R^1$=$R^4$=$R^5$=H, $R^2$=$R^3$=methyl, $X^1$=NH, $X^2$=CH$_2$, In other embodiments of the invention, compounds of Formula 1 include substituents where;
$R^4$ and $R^5$ taken together are —CH$_2$—(CH$_2$)$_n$—CH$_2$— and;
$R^1$=methyl, $R^2$=$R^3$=H, n=0, $X^1$=NH, $X^2$=CH$_2$;
$R^1$=methyl, $R^2$=$R^3$=H, n=2, $X^1$=NH, $X^2$=CH$_2$;
$R^1$=allyl, $R^2$=$R^3$=H, n=0, $X^1$=NH, $X^2$=CH$_2$;
$R^1$=allyl, $R^2$=$R^3$=H, n=2, $X^1$=NH, $X^2$=CH$_2$.
$R^1$=methyl, $R^2$=$R^3$=H, n=3, $X^1$=NH, $X^2$=CH$_2$;
$R^1$=allyl, $R^2$=$R^3$=H, n=3, $X^1$=NH, $X^2$=CH$_2$.

In still other embodiments of the invention, compounds of Formula 1 include substituents where $R^1$=methyl or allyl, $R^2$=$R^3$=$R^4$=H and $R^5$ is selected from the group consisting of the side chains of the amino acids: alanine, arginine, asparagine, aspartic acid, cysteine, glutamic acid, glutamine, histidine, isoleucine, leucine, lysine, methionine, proline, serine, threonine, tryptophan, tyrosine, valine, norvaline, norleucine, citruline, ornithine, homocysteine, homoserine, alloisoleucine, isovaline, sarcosine and the like.

In yet further embodiments of the invention, compounds of Formula 1 include substituents where:

$R^1$=methyl, $R^2$=$R^3$=methyl, $R^4$=$R^5$=H, $X^1$=NH and $X^2$=S;
$R^1$=allyl, $R^2$=$R^3$=methyl, $R^4$=$R^5$=H, $X^1$=NH and $X^2$=S.

Those with skill in the art will appreciate that the above structural representations can contain chiral centres, the number of which will depend on the different substituents. The chirality may be either R or S at each centre. The structural drawings can represent only one of the possible tautomeric, conformational diastereomeric or enantiomeric forms, and it should be understood that the invention encompasses any tautomeric, conformational isomeric diastereomeric or enantiomeric form, which exhibits biological or pharmacological activity as described herein.

Pharmacology and Utility

Cyclic Glycyl-2-Allyl proline (cG-2-AllylP) is described in U.S. Utility application Ser. No. 11/399,974 filed Apr. 7, 2006, entitled "Cyclic G-2Allyl Proline in Treatment of Parkinson's Disease," now U.S. Pat. No. 7,776,876, issued Aug. 17, 2010, U.S. Utility application Ser. No. 10/570,395, filed Mar. 2, 2006 entitled "Neuroprotective Bicyclic Compounds and Methods for Their Use", PCT International Patent Application No: PCT/US2004/028308, entitled Neuroprotective Bicyclic Compounds and methods for Their Use, and U.S. Provisional Patent Application Ser. No. 60/499,956 filed Sep. 3, 2003, entitled "Neuroprotective Bicyclic Compounds and Methods for Their Use". Each of the above patent applications and the patent is expressly incorporated herein fully by reference.

Certain aspects of this invention include the use of cyclic G-2-AllylP in treatment of cognitive impairment associated with aging with neurodegenerative conditions or in situations in which cognitive impairment is found with no apparent neurodegeneration.

Scopolamine is commonly used in animal models of cholinergic hypofunction associated with Alzheimer's disease. The functional deficits observed after scopolamine treatment include those found in human patients with Alzheimer's disease. Thus, scopolamine treatment is reasonably predictive of cognitive impairment found in human diseases. Additionally, scopolamine treatment mimics cognitive disfunction in humans who do not have neurodegenerative disorders.

cG-2-AllylP administered to animals treated with scopolamine-induced cognitive dysfunction produces clinical improvement in those animals, similar to the therapeutic improvement observed in people suffering from cholinergic hypofunction. For example, cholinergic hypofunction associated with Alzheimer's disease. Thus, studies of effects of Cyclic G-2-AllylP scopolamine treated animals are reasonably predictive of effects observed in human beings suffering from cholinergic dysfunction.

Such other agents may be selected from the group consisting of for example, growth factors and associated derivatives, e.g., insulin-like growth factor-I (IGF-I), insulin-like growth factor-II (IGF-II), the tripeptide GPE, transforming growth factor-β1, activin, growth hormone, nerve growth factor, growth hormone binding protein, and/or IGF-binding proteins. Additional compounds include Glycyl-2-Methyl Prolyl Glutamate and/or other compounds disclosed in U.S. patent application Ser. No. 10/155,864, now U.S. Pat. No. 7,041,314, issued May 9, 2006, expressly incorporated herein fully by reference.

Therapeutic Applications

Compositions and methods of the invention find use in the treatment of animals, such as human patients, suffering from cognitive impairment. Still more generally, the compositions and methods of the invention find use in the treatment of mammals, such as human patients, suffering from memory impairment, mild cognitive impairment, dementia, including dementia including dementias resulting from cerebral atrophy associated with Alzheimer's disease, Lewy-bodies disease, frontotemporal lobar degeneration, Pick's disease; vascular narrowing or blockage in the brain (i.e. vascular dementia also known as multi-infarct dementia); Huntington's disease, Parkinson's disease; head trauma; HIV infection or Down's syndrome.

Pharmaceutical Compositions and Administration

Cyclic G-2-AllylP can be administered as part of a medicament or pharmaceutical preparation. This can involve combining a compound of the invention with any pharmaceutically appropriate carrier, adjuvant or excipient. The selection of the carrier, adjuvant or excipient will of course usually be dependent upon the route of administration to be employed.

In general, compounds of this invention will be administered in therapeutically effective amounts by any of the usual modes known in the art, either singly or in combination with other conventional therapeutic agents for the disease being treated. A therapeutically effective amount may vary widely depending on the disease or injury, its severity, the age and relative health of the animal being treated, the potency of the compound(s), and other factors. As anti-apoptotic and anti-necrotic agents, therapeutically effective amounts of cyclic G-2-AllylP may range from 0.001 to 100 milligrams per kilogram mass of the animal, with lower doses such as 0.001 to 0.1 mg/kg being appropriate for administration through the cerebrospinal fluid, such as by intracerebroventricular administration, and higher doses such as 1 to 100 mg/kg being appropriate for administration by methods such as oral, systemic (e.g. transdermal), or parenteral (e.g. intravenous) administration. A person of ordinary skill in the art will be able without undue experimentation, having regard to that skill and this disclosure, to determine a therapeutically effective amount of a compound of this invention for a given disease or injury.

Cyclic G-2-AllylP may be administered peripherally via any peripheral route known in the art. These can include parenteral routes for example injection into the peripheral circulation, subcutaneous, intraorbital, ophthalmic, intraspinal, intracisternal, topical, infusion (using e.g. slow release devices or minipumps such as osmotic pumps or skin patches), implant, aerosol, inhalation, scarification, intraperitoneal, intracapsular, intramuscular, intranasal, oral, buccal, transdermal, pulmonary, rectal or vaginal. The compositions can be formulated for parenteral administration to humans or other mammals in therapeutically effective amounts (e.g. amounts which eliminate or reduce the patient's pathological condition) to provide therapy for the neurological diseases described above.

Desirably, if possible, when administered as anti-apoptotic and anti-necrotic agent, cyclic G-2-AllylP can be administered orally. The amount of a compound of this invention in the composition may vary widely depending on the type of composition, size of a unit dosage, kind of excipients, and other factors well known to those of ordinary skill in the art.

In general, the final composition may comprise from 0.0001 percent by weight (% w) to 10% w of the compound of this invention, preferably 0.001% w to 1% w, with the remainder being the excipient or excipients.

Other convenient administration routes include subcutaneous injection (e.g. dissolved in a physiologically compatible carrier such as 0.9% sodium chloride) or direct administration to the CNS. Using stereotactic devices and accurate maps of an animals' CNS, a compound may be injected directly into a site of neural damage. Such routes of administration may be especially desired in situations in which perfusion of that location is compromised either by decreased vascular perfusion or by decreased cerebral spinal fluid (CSF) flow to that area. Examples include administration by lateral cerebroventricular injection or through a surgically inserted shunt into the lateral cerebroventricle of the brain of the patient, intraveneously, direct injection into the desired location or other routes.

The effective amount of compound in the CNS may be increased by administration of a pro-drug form of a compound, which comprises a compound of the invention and a carrier, where the carrier is joined to a compound of the invention by a linkage which is susceptible to cleavage or digestion within the patient. Any suitable linkage can be employed which will be cleaved or digested following administration.

However, there is no intention on the part of the applicants to exclude other forms of administration.

In further embodiments of the invention, restoring nerve function in an animal can comprise administering a therapeutic amount of cyclic G-2-AllylP in combination with another neuroprotective agent, selected from, for example, growth factors and associated derivatives (insulin-like growth factor-I (IGF-I), insulin-like growth factor-II (IGF-II), transforming growth factor-$\beta$1, activin, growth hormone, nerve growth factor, growth hormone binding protein, IGF-binding proteins (especially IGFBP-3), basic fibroblast growth factor, acidic fibroblast growth factor, the hst/Kfgk gene product, FGF-3, FGF-4, FGF-6, keratinocyte growth factor, androgen-induced growth factor. Additional members of the FGF family include, for example, int-2, fibroblast growth factor homologous factor-1 (FHF-1), FHF-2, FHF-3 and FHF-4, karatinocyte growth factor 2, glial-activating factor, FGF-10 and FGF-16, ciliary neurotrophic factor, brain derived growth factor, neurotrophin 3, neurotrophin 4, bone morphogenetic protein 2 (BMP-2), glial-cell line derived neurotrophic factor, activity-dependant neurotrophic factor, cytokine leukaemia inhibiting factor, oncostatin M, interleukin), $\alpha$-, $\beta$-, $\gamma$-, or consensus interferon, and TNF-$\alpha$. Other forms of neuroprotective therapeutic agents include, for example, clomethiazole; kynurenic acid, Semax, tacrolimus, L-threo-1-phenyl-2-decanoylamino-3-morpholino-1-propanol, andrenocorticotropin-(4-9) analogue (ORG 2766) and dizolcipine (MK-801), selegiline; glutamate antagonists such as, NPS1506, GV1505260, MK-801, GV150526; AMPA antagonists such as 2,3-dihydroxy-6-nitro-7-sulfamoylbenzo(f)quinoxaline (NBQX), LY303070 and LY300164; anti-inflammatory agents directed against the addressin MAd-CAM-1 and/or its integrin $\alpha$4 receptors ($\alpha$4$\beta$1 and $\alpha$4$\beta$7), such as anti-MAdCAM-1mAb MECA-367 (ATCC accession no. HB-9478).

Cyclic G-2-AllylP is suitably administered by a sustained-release system. Suitable examples of sustained-release compositions include semi-permeable polymer matrices in the form of shaped articles, e.g., films, or microcapsules. Sustained-release matrices include polylactides (U.S. Pat. No. 3,773,919; EP 58,481), copolymers of L-glutamic acid and gamma-ethyl-L-glutamate (Sidman et al., 1983, *Biopolymers:* 22: 547-56), poly(2-hydroxyethyl methacrylate) (Langer et al., 1981, *J. Biomed. Mater. Res.:* 15: 267), ethylene vinyl acetate (Langer et al., 1981, *J. Biomed. Mater. Res.:* 15: 267), or poly-D-(−)-3-hydroxybutyric acid (EP 133,988). Sustained-release compositions also include a liposomally entrapped compound. Liposomes containing the compound are prepared by methods known per se: DE 3,218,121, EP 52,322, EP 36,676, EP 88,046, EP 143,949, EP 142,641, Japanese Pat. Appln. 83-118008, U.S. Pat. Nos. 4,485,045 and 4,544,545, and EP 102,324. Ordinarily, the liposomes are of the small (from or about 200 to 800 Angstroms) unilamellar type in which the lipid content is greater than about 30 mol percent cholesterol, the selected proportion being adjusted for the most efficacious therapy.

For parenteral administration, in one embodiment cyclic G-2-AllylP is formulated generally by mixing each at the desired degree of purity, in a unit dosage injectable form (solution, suspension, or emulsion), with a pharmaceutically, or parenterally, acceptable carrier, i.e., one that is non-toxic to recipients at the dosages and concentrations employed and is compatible with other ingredients of the formulation.

Generally, the formulations are prepared by contacting cyclic G-2-AllylP uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, a buffered solution, and dextrose solution. Non-aqueous vehicles such as fixed oils and ethyl oleate are also useful herein.

A carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; glycine; amino acids such as glutamic acid, aspartic acid, histidine, or arginine; monosaccharides, disaccharides, and other carbohydrates including cellulose or its derivatives, glucose, mannose, trehalose, or dextrins; chelating agents such as EDTA; sugar alcohols such as mannitol or sorbitol; counter-ions such as sodium; nonionic surfactants such as polysorbates, poloxamers, or polyethylene glycol (PEG); and/or neutral salts, e.g., NaCl, KCl, $MgCl_2$, $CaCl_2$, etc.

Cyclic G-2-AllylP is typically formulated in such vehicles at a pH of from or about 4.5 to 8. It will be understood that use of certain of the foregoing excipients, carriers, or stabilizers will result in the formation of salts of the compound. The final preparation may be a stable liquid or lyophilized solid.

Formulations of cyclic G-2-AllylP in pharmaceutical compositions can also include adjuvants. Typical adjuvants which may be incorporated into tablets, capsules, and the like are a binder such as acacia, corn starch, or gelatin; an excipient such as microcrystalline cellulose; a disintegrating agent like corn starch or alginic acid; a lubricant such as magnesium stearate; a sweetening agent such as sucrose or lactose; a flavouring agent such as peppermint, wintergreen, or cherry. When dosage forms are tablets, cyclic G-2-AllylP compositions can include binders and optionally, a smooth coating. When the dosage form is a capsule, in addition to the above materials, it may also contain a liquid carrier such as a fatty oil. Other materials of various types may be used as coatings or as modifiers of the physical form of the dosage unit. A syrup or elixir may contain the active compound, a sweetener such as sucrose, preservatives like propyl paraben, a colouring agent, and a flavouring agent such as cherry. Sterile compositions for injection can be formulated according to conventional pharmaceutical practice. For example, dissolution or suspension of the active compound in a vehicle such as water or naturally occurring vegetable oil like sesame, peanut, or cottonseed oil or a synthetic fatty vehicle like ethyl oleate or the like may be desired. buffers, preservatives, antioxidants, and the like can be incorporated according to accepted pharmaceutical practice.

For injection, intraventricular administration and other invasive routes of administration, cyclic G-2-AllylP must be sterile. Sterility may be accomplished by any method known in the art, for example filtration through sterile filtration membranes (e.g., 0.2 micron membranes). Therapeutic compositions generally are placed into a container having a sterile access port, for example, an intravenous solution bag or vial having a stopper able to be pierced by a hypodermic injection needle.

A pharmaceutical formulation containing cyclic G-2-AllylP ordinarily will be stored in unit or multi-dose containers, for example, in sealed ampoules or vials, as an aqueous solution or as a lyophilized formulation for reconstitution. As an example of a lyophilized formulation, 10 mL vials are filled with 5 mL of sterile-filtered 1% (w/v) aqueous solution of compound, and the resulting mixture is lyophilized. The infusion solution is prepared by reconstituting the lyophilized compound using bacteriostatic Water-for-Injection. It can be readily appreciated that other dosage forms and types of preparations can be used, and all are considered to be part of this invention.

Preparation of the Compounds

Starting materials and reagents used in preparing cyclic G-2-AllylP are either available from commercial suppliers such as Aldrich Chemical Company (Milwaukee, Wis.), Bachem (Torrance, Calif.), Sigma (St. Louis, Mo.), or are prepared by methods well known to the person of ordinary skill in the art following procedures described in such references as Fieser and Fieser's Reagents for Organic Synthesis, vols 1-17, John Wiley and Sons, New York, N.Y., 1991; Rodd's Chemistry of Carbon Compounds, vols. 1-5 and supplements, Elsevier Science Publishers, 1989; Organic Reactions, vols. 1-40, John Wiley and Sons, New York, N.Y., 1991; March J; Advanced Organic Chemistry, $4^{th}$ ed. John Wiley and Sons, New York, N.Y., 1992; and Larock: Comprehensive Organic Transformations, VCH Publishers, 1989. In most instances, amino acids and their esters or amides, and protected amino acids, are widely commercially available; and the preparation of modified amino acids and their amides or esters are extensively described in the chemical and biochemical literature and thus well-known to persons of ordinary skill in the art.

Starting materials, intermediates, and final products this invention may be isolated and purified using conventional techniques, including filtration, distillation, crystallization, chromatography, and the like. They may be characterized using conventional methods, including physical constants and spectral data.

Cyclic G-2-AllylP is a cyclic dipeptide (bicyclic 2,5-diketopiperazine). In general, cyclic G-2-AllylP may be prepared by methods such as are already well-known to persons of ordinary skill in the art of peptide and modified peptide synthesis, following the reaction schemes set forth in the Figures following this specification, or by following other methods well-known to those of ordinary skill in the art of the synthesis of peptides and analogues. See for example, Bodanzsky: Principles of Peptide Synthesis, Berlin, N.Y.: Springer-Verlag 1993. Synthesis of the diketopiperazine compounds of this invention may be by solution-phase synthesis as discussed in the Examples or via the solid-phase synthesis method exemplified by Merrifield et al. 1963 *J. Amer. Chem. Soc.:* 85, 2149-2156. Solid phase synthesis may be performed using commercial peptide synthesizers, such as the Applied Biosystems Model 430A, using the protocols established for the instrument.

Specific examples of diketopiperazine synthesis can be found in the Examples following and in, for example, Fischer, 2003, *J. Peptide Science:* 9: 9-35 and references therein. A person of ordinary skill in the art will have no difficulty, taking account of that skill and the knowledge available, and of this disclosure, in developing one or more suitable synthetic methods for compounds of this invention.

The choice of appropriate protecting groups for the method chosen (solid-phase or solution-phase), and of appropriate substrates if solid-phase synthesis is used, will be within the skill of a person of ordinary skill in the art. Appropriate protecting groups for peptide synthesis include t-butyloxycarbonyl (Boc), fluorenylmethyloxycarbonyl (Fmoc), Benzyl (Bzl), t-amyloxycarbonyl (Aoc), tosyl (Tos), benzyloxycarbonyl (Z or Cbz), o-bromo-benzyloxycarbonyl (BrZ) and the like. Additional protecting groups are identified in Goodman M. (ed.), "Synthesis of Peptides and Peptidomimetics" in Methods of organic chemistry (Houben-Weyl) (Workbench Edition, E22a,b,c,d,e; 2004; Georg Thieme Verlag, Stuttgart, New York).

The choice of coupling agent for the method chosen will also be within the skill of a person of ordinary skill in the art. Suitable coupling agents include DCC(N,N'-Dicyclohexylcarbodiimide), Bop (Benzotriazole-1-yl-oxy-tris-(dimethylamino)-phosphonium hexafluorophosphate), PyBop (Benzotriazol-1-yl-oxytripyrrolidinophosphonium hexafluorophosphate), BopCl (bis(2-oxo-3-oxazolidinyl) phosphinic chloride), 2-Chloro-1,3-dimethylimidazolidinium hexafluorophosphate (CIP) and the like. Other compounds may be used in the synthesis e.g. to prevent racemisation, such as HOBt (N-Hydroxybenzotriazole) and HOAt (1-Hydroxy-7-azabenzotriazole).

All patent and literature references cited throughout the specification are expressly incorporated by reference in their entirety as if each had been separately so incorporated.

EXAMPLES

The present invention is further illustrated by the following examples. These examples are offered by way of illustration only and are not intended to limit the scope of the invention.

General Methods

Flash chromatography was performed using Scharlau 60 (40-60 µm mesh) silica gel. Analytical thin layer chromatography was carried out on 0.20 mm pre-coated silica gel plates (ALUGRAM® SIL G/UV$_{254}$) and compounds visualized using UV fluorescence, or heating of plates dipped in potassium permanganate in alkaline solution.

Melting points in degrees Celsius (° C.) were determined on an Electrothermal® melting point apparatus and are uncorrected.

Optical rotations were measured at 20° C. on a Perkin Elmer 341 polarimeter using 10 cm path length cells and are given in units of $10^{-1}$ degcm$^2$ g$^{-1}$. Samples were prepared in the solvent indicated at the concentration specified (measured in g/100 cm$^3$). IR spectra were recorded on a Perkin Elmer Spectrum One FT-IR spectrometer. The samples were prepared as thin films on sodium chloride discs or as solids in potassium bromide discs. A broad signal indicated by br. The frequencies (υ) as absorption maxima are given in wavenumbers (cm$^{-1}$).

NMR spectra were recorded on a Bruker AVANCE DRX400 ($^1$H, 400 MHz; $^{13}$C, 100 MHz) or a Bruker AVANCE 300 ($^1$H, 300 MHz; $^{13}$C, 75 MHz) spectrometer at ambient temperatures. For $^1$H NMR data chemical shifts are described in parts per million downfield from SiMe$_4$ and are reported consecutively as position ($\delta_H$), relative integral, multiplicity (s=singlet, d=doublet, t=triplet, dd=doublet of doublets, m=multiplet, br=broad), coupling constant (J/Hz) and assignment. For $^{13}$C NMR data, chemical shifts are described in parts per million relative to CDCl$_3$ and are reported consecutively as position ($\delta_C$), degree of, hybridization as determined by DEPT experiments, and assignment. $^1$H NMR spectra were referenced internally using SiMe$_4$ (δ 0.00) or CDCl$_3$ (δ 7.26). $^{13}$C NMR spectra were referenced internally using CDCl$_3$ (δ 77.0). When two sets of peaks arise in the NMR spectra due to different conformations around the glycine-proline amide bond, the chemical shift for the minor cis conformer is marked with an asterisk (*).

Accurate mass measurements were recorded on a VG-70SE mass spectrometer. Hexane and dichloromethane were distilled prior to use. Methanol was dried using magnesium turnings and iodine, and distilled under nitrogen. Triethylamine was dried over calcium hydride and distilled under nitrogen.

Example 1

Synthesis of (8aS)-Methyl-hexahydropyrrolo[1,2-a]pyrazine-1,4-dione (Cyclic G-2MeP)

Scheme 1: Reagents, conditions and yields:

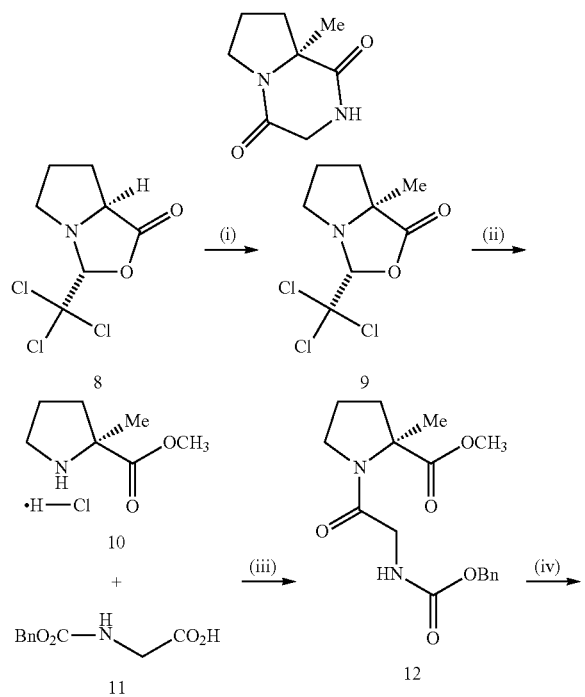

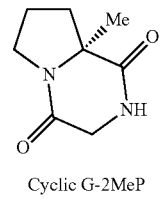

Cyclic G-2MeP (i) LDA, THF, -78° C., iodomethane, -78 -> -50° C., 2 h (63%); (ii) SOCl$_2$, CH$_3$OH, reflux, N$_2$, 2.5 h (98%); (iii) Et$_3$N, BoPCl, CH$_2$Cl$_2$, RT, N$_2$, 20.5 h (78%); (iv) 10% Pd/C, CH$_3$OH, RT, 15 h (98%).

(2R,5S)-4-Methyl-2-trichloromethyl-1-aza-3-oxabicyclo[3.3.0]octan-4-one 9 n-BuLi (1.31M, 4.68 cm$^3$, 6.14 mmol) was added dropwise to a stirred solution of diisopropylamine (0.86 cm$^3$, 6.14 mmol) in dry tetrahydrofuran (10 cm$^3$) at -78° C. under an atmosphere of nitrogen. The solution was stirred for 5 min, warmed to 0° C. and stirred for 15 min. The solution was then added dropwise to a solution of oxazolidinone 8 (1.00 g, 4.09 mmol) in dry tetrahydrofuran (20 cm$^3$) at -78° C. over 20 min (turned to a dark brown colour), stirred for a further 30 min then iodomethane (0.76 cm$^3$, 12.3 mmol) was added dropwise over 5 min. The solution was warmed to -50° C. over 2 h. Water (15 cm$^3$) was added and the solution warmed to room temperature and extracted with chloroform (3×40 cm$^3$). The combined organic extracts were dried (MgSO$_4$), filtered and evaporated to dryness in vacuo to give a dark brown semi-solid. Purification of the residue by flash column chromatography (15% ethyl acetate-hexane) afforded oxazolidinone 9 (0.67 g, 63%) as a pale yellow solid: mp 55-57° C. (lit., 57-60° C.); δ$_H$ (300 MHz, CDCl$_3$) 1.53 (3H, s, CH$_3$), 1.72-2.02 (3H, m, Proβ-H and Proγ-H$_2$), 2.18-2.26 (1H, m, Proβ-H), 3.15-3.22 (1H, m, Proδ-H), 3.35-3.44 (1H, m, Proδ-H) and 4.99 (1H, s, NCH).

Methyl L-2-methylprolinate hydrochloride 10 a) Using Acetyl Chloride

Oxazolidinone 9 (0.60 g, 2.33 mmol) was dissolved in dry methanol (15 cm$^3$) under an atmosphere of nitrogen and acetyl chloride (0.33 cm$^3$, 4.66 mmol) was added dropwise to the ice-cooled solution. The solution was heated under reflux for 4.5 h, then the solvent removed under reduced pressure to give a brown oil which was purified by flash column chromatography (10% CH$_3$OH—CH$_2$Cl$_2$) affording the hydrochloride 10 (0.2 g, 48%) as a flaky white solid: mp 107-109° C. (lit., 106-108° C.); δ$_H$ (300 MHz, CDCl$_3$) 1.81 (3H, s, CH$_3$), 1.93-2.14 (3H, m, Proβ-H$_A$H$_B$ and Proγ-H$_2$), 2.33-2.39 (1H, m, Proβ-H$_A$H$_B$), 3.52-3.56 (2H, m, Proδ-H$_2$) and 3.82 (3H, s, CO$_2$CH$_3$).

b) Using Thionyl Chloride

An ice-cooled solution of oxazolidinone 9 (53 mg, 0.21 mmol) in dry methanol (1 cm$^3$) was treated dropwise with thionyl chloride (0.045 cm$^3$, 0.62 mmol). The solution was heated under reflux for 2.5 h, cooled and the solvent removed under reduced pressure to yield a brown oil. The oil was dissolved in toluene (5 cm$^3$), concentrated to dryness to remove residual thionyl chloride and methanol then purified by flash column chromatography (10% CH₃OH—CH₂Cl₂) to afford the hydrochloride 10 (16 mg, 43%) as a flaky white solid. The ¹H NMR assignments were in agreement with those reported above.

Methyl-N-benzyloxycarbonyl-glycyl-L-2-methylprolinate 12

Dry triethylamine (0.27 cm³, 1.96 mmol) was added dropwise to a solution of hydrochloride 10 (0.11 g, 0.61 mmol) and N-benzyloxycarbonyl-glycine 11 (98.5%) (0.17 g, 0.79 mmol) in dry dichloromethane (35 cm³) under an atmosphere of nitrogen at room temperature, and the reaction mixture stirred for 10 min. Bis(2-oxo-3-oxazolidinyl)phosphinic chloride (BoPCl, 97%) (0.196 g, 0.77 mmol) was added and the resultant colourless solution was stirred for 20.5 h. The solution was washed successively with 10% aqueous hydrochloric acid (30 cm³) and saturated aqueous sodium hydrogen carbonate (30 cm³), dried (MgSO₄), filtered and evaporated to dryness in vacuo. Purification of the resultant residue by flash column chromatography (50-80% ethyl acetate-hexane; gradient elution) yielded dipeptide 12 (0.18 g, 92%) as a colourless oil. Amide 12 was shown to exist as a 98:2 trans:cis mixture of conformers by ¹³C NMR analysis (the ratio was estimated from the relative intensities of the resonances at δ20.8 and 23.5 assigned to the Proγ-C atoms of the minor and major conformers, respectively): [α]$_D$ −33.0 (c 1.0 in MeOH); ν$_{max}$ (film)/cm⁻¹ 3406, 2952, 1732, 1651, 1521, 1434, 1373, 1329, 1310, 1284, 1257, 1220, 1195, 1172, 1135, 1107, 1082, 1052, 1029, 986, 965, 907, 876, 829, 775, 738 and 699; δ$_H$ (300 MHz, CDCl₃) 1.49 (3H, s, CH₃), 1.77-2.11 (4H, m, Proβ-H₂ and Proγ-H₂), 3.43-3.48 (2H, m, Proδ-H₂), 3.61 (3H, s, OCH₃), 3.85-3.89 (2H, m, Glyα-H₂), 5.04 (2H, s, PhCH₂), 5.76 (1H, br s, N—H) and 7.21-7.28 (5H, s, ArH); δ$_C$ (75 MHz, CDCl₃) 13.8* (CH₃, Proα-CH₃), 21.1 (CH₃, Proα-CH₃), 20.8* (CH₂, Proγ-C), 23.5 (CH₂, Proγ-C), 38.0 (CH₂, Proβ-C), 40.8* (CH₂, Proβ-C), 43.3 (CH₂, Glyα-C), 45.5* (CH₂, Glyα-C), 46.6 (CH₂, Proδ-C), 48.7* (CH₂, Proδ-C), 51.9* (CH₃, OCH₃), 52.1 (CH₃, OCH₃), 60.0* (quat., Proα-C), 66.0 (quat., Proα-C), 66.3 (CH₂, PhCH₂), 68.6* (CH₂, PhCH₂), 127.5 (CH, Ph), 127.6 (CH, Ph), 127.9* (CH, Ph), 128.1 (CH, Ph), 128.3* (CH, Ph), 136.2 (quat., Ph), 155.9 (quat., NCO₂), 166.0 (quat., Gly-CON), 169.4* (quat., Gly-CON) and 173.6 (quat., CO₂CH₃); m/z (EI+) 334.1535 (M⁺. C₁₇H₂₂N₂O₅ requires 334.1529).

(8aS)-Methyl-hexahydropyrrolo[1,2-a]pyrazine-1,4-dione (Cyclic G-2-MeP)

To a solution of dipeptide 12 (0.167 g, 0.51 mmol) in methanol (8.0 cm³) was added 10% Pd on activated charcoal (8.1 mg, 0.076 mmol) and the vessel flushed with hydrogen gas. The resulting suspension was stirred vigorously under an atmosphere of hydrogen for 15 h. The mixture was then filtered through a Celite pad then a short plug of silica gel with methanol, and the solvent removed under reduced pressure to produce cyclic G-2MeP (83 mg, 98%) as a yellow solid: mp 133-135° C.; [α]$_D$ −128.1 (c 0.52 in MeOH); δ$_H$ (300 MHz, CDCl₃) 1.36 (3H, s, CH₃), 1.87-2.01 (3H, m, Proβ-H$_A$H$_B$ and Proγ-H₂), 2.07-2.21 (1H, m, Proβ-H$_A$H$_B$), 3.45-3.64 (2H, m, Proδ-H₂), 3.82 (1H, dd, J 17.1 and 4.1, CH$_A$H$_B$NH), 3.99 (1H, d, J 17.1, CH$_A$H$_B$NH) and 7.66 (1H, br s, N—H); δ$_C$(75 MHz, CDCl₃) 20.2 (CH₂, Proγ-C), 23.2 (CH₃, Proα-CH₃), 35.0 (CH₂, Proβ-C), 44.7 (CH₂, Proδ-C), 45.9 (CH₂, CH₂NH), 63.8 (quat., Proα-C), 163.3 (quat., NCO) and 173.3 (quat., CONH); m/z (EI+) 168.08986 (M⁺. C₈H₁₂N₂O₂ requires 168.08988).

Example 2

Synthesis of (8aS)-Methyl-spiro[cyclohexane-1,3 (4H)-tetrahydropyrrolo[1,2-a]pyrazine]-1,4(2H)-dione (Cyclic cyclohexyl-G-2-MeP)

Scheme 2: Reagents, conditions and yields:

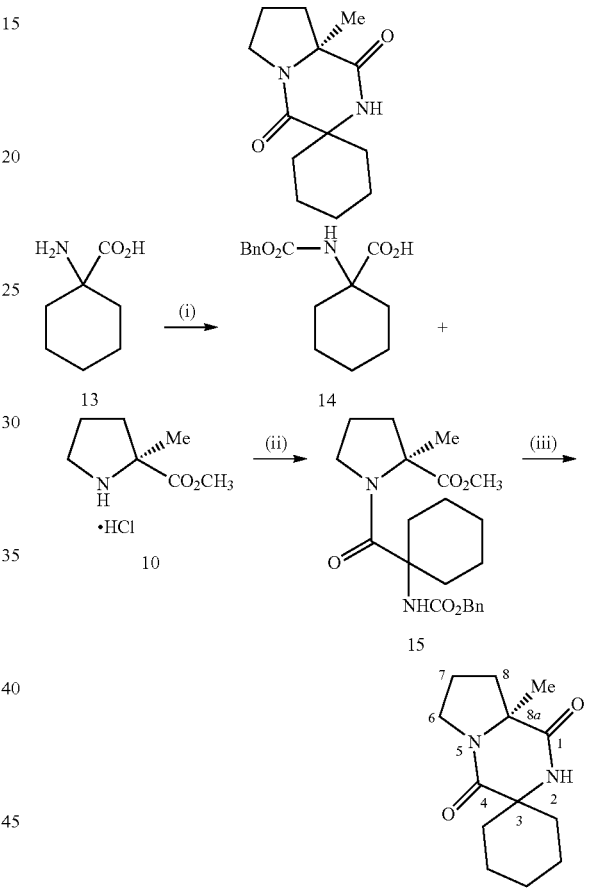

Cyclic cyclohexyl-G-2MeP (i) BnO₂CCl, Na₂CO₃, H₂O-dioxane (3:1), 19 h, 96%, (ii) Et₃N, HOAt, CIP, 1,2-dichloroethane, reflux, N₂, 19 h (23%); (iii) 10% Pd/C, CH₃OH, RT, 17 h (65%).

N-Benzyloxycarbonyl-1-aminocyclohexane-1-carboxylic acid (14)

To a suspension of 1-aminocyclohexanecarboxylic acid 13 (0.72 g, 5.02 mmol) and sodium carbonate (1.6 g, 15.1 mmol) were dissolved in water-dioxane (21 cm³, 3:1) was added benzyl chloroformate (0.79 cm³, 5.52 mmol) was added dropwise and the solution was stirred at room temperature for 19.5 h. The aqueous layer was washed with diethyl ether (60 cm³), acidified with 2 M HCl and extracted with ethyl acetate (2×60 cm³). The organic layers were combined, dried (MgSO₄), filtered and evaporated under reduced pressure to produce a colourless oil, which solidified on standing to crude carbamate 14 (1.23 g, 88%) as a white solid: mp 152-154° C. (lit., 148-150° C.); δ$_H$ (400 MHz, CDCl$_3$) 1.27-1.56 (3H, m, 3× cyclohexyl-H), 1.59-1.73 (3H, m, 3× cyclohexyl-H), 1.85-1.91 (2H, m, 2× cyclopentyl-H), 2.05-2.09 (2H, m, 2× cyclopentyl-H), 5.02 (1H, br s, N—H), 5.12 (2H, s, OCH$_2$Ph) and 7.27-7.36 (5H, s, Ph); δ$_C$ (100 MHz, CDCl$_3$) 21.1 (CH$_2$, 2× cyclohexyl-C), 25.1 (CH$_2$, 2× cyclohexyl-C), 32.3 (CH$_2$, cyclohexyl-C), 59.0 (quat., 1-C), 67.1 (CH$_2$, OCH$_2$Ph), 128.1 (CH, Ph), 128.2 (CH, Ph), 128.5 (CH, Ph), 136.1 (quat., Ph), 155.7 (quat., NCO$_2$) and 178.7 (quat., CO$_2$H).

Methyl-N-benzyloxycarbonyl-cyclohexyl-glycyl-L-2-methylprolinate (15)

Dry triethylamine (0.21 cm$^3$, 1.5 mmol) was added dropwise to a solution of hydrochloride 10 (84.0 mg, 0.47 mmol), carboxylic acid 14 (0.17 g, 0.61 mmol) and 1-hydroxy-7-azabenzotriazole (16 mg, 0.12 mmol) in dry 1,2-dichloroethane (26 cm$^3$) under an atmosphere of nitrogen at room temperature, and the reaction mixture stirred for 10 min. 2-Chloro-1,3-dimethylimidazolidinium hexafluorophosphate (0.13 g, 0.47 mmol) was added and the resultant solution heated under reflux for 21 h, then washed successively with 10% aqueous hydrochloric acid (30 cm$^3$) and saturated aqueous sodium hydrogen carbonate (30 cm$^3$), dried (MgSO$_4$), filtered and evaporated to dryness in vacuo. Purification of the resultant residue by flash column chromatography (40-50% ethyl acetate-hexane; gradient elution) yielded amide 15 (16 mg, 9%) as a white solid. Amide 15 was shown to exist as a 11:1 trans:cis mixture of conformers by $^{13}$C NMR analysis (the ratio was estimated from the relative intensities of the resonances at δ 41.3 and 48.2 assigned to the Proδ-C atoms of the minor and major conformers, respectively): mp 219-222° C.; [α]$_D$ −44.9 (c 1.31 in CH$_2$Cl$_2$); v$_{max}$ (film)/cm$^{-1}$ 3239, 2927, 1736, 1707, 1617, 1530, 1450, 1403, 1371, 1281, 1241, 1208, 1194, 1165, 1150, 1132, 1089, 1071, 1028, 984, 912, 796, 749, 739 and 699; δ$_H$ (400 MHz, CDCl$_3$) 1.24-2.10 (17H, m, Proα-CH$_3$, Proβ-H$_2$, Proγ-H$_2$ and 5× cyclohexyl-H$_2$), 3.25-3.48 (1H, br m, Proδ-H$_A$H$_B$), 3.61-3.87 (4H, br m, OCH$_3$ and Proδ-H$_A$H$_B$), 4.92-5.19 (3H, m, N—H and OCH$_2$Ph) and 7.35-7.37 (5H, s, Ph); δ$_C$ (100 MHz, CDCl$_3$) 21.26 (CH$_2$, cyclohexyl-C), 21.33 (CH$_2$, cyclohexyl-C), 21.7 (CH$_3$, Proα-CH$_3$), 24.8 (CH$_2$, cyclohexyl-C), 25.0 (CH$_2$, Proγ-C), 29.4* (CH$_2$, cyclohexyl-C), 29.7* (CH$_2$, cyclohexyl-C), 31.1 (CH$_2$, cyclohexyl-C), 31.6 (CH$_2$, cyclohexyl-C), 31.9* (CH$_2$, cyclohexyl-C), 32.2* (CH$_2$, cyclohexyl-C), 32.8* (CH$_2$, cyclohexyl-C), 37.3 (CH$_2$, Proβ-C), 41.4* (CH$_2$, Proδ-C), 48.2 (CH$_2$, Proδ-C), 52.1 (CH$_3$, OCH$_3$), 59.1 (quat., Glyα-C), 66.7 (CH$_2$, OCH$_2$Ph), 67.3* (CH$_2$, OCH$_2$Ph), 67.4 (quat., Proα-C), 128.0* (CH, Ph), 128.1* (CH, Ph), 128.3 (CH, Ph), 128.5 (CH, Ph), 128.7 (CH, Ph), 136.6 (quat., Ph), 153.7 (quat., NCO$_2$), 171.0 (quat., Gly-CO) and 174.8 (quat., CO$_2$CH$_3$); m/z (EI+) 402.2151 (M$^+$. C$_{22}$H$_{30}$N$_2$O$_5$ requires 402.2155).

(8aS)-Methyl-spiro[cyclohexane-1,3(4H)-tetrahydropyrrolo[1,2-a]pyrazine]-1,4(2H)-dione (Cyclic cyclohexyl-G-2-MeP)

To a solution of amide 15 (40 mg, 0.01 mmol) in methanol (3.3 cm$^3$) was added 10% Pd on activated charcoal (1.6 mg, 0.015 mmol) and the vessel flushed with hydrogen gas. The resulting suspension was stirred vigorously under an atmosphere of hydrogen for 61.5 h, then filtered through a Celite™ pad with methanol (15 cm$^3$). The filtrate was concentrated to dryness under reduced pressure to produce a yellow semi-solid which was purified by reverse-phase C18 flash column chromatography (0-10% CH$_3$CN/H$_2$O; gradient elution) to produce cyclic cyclohexyl-G-2MeP (19 mg, 81%) as a white solid: mp 174-177° C.; [α]$_D$ −63.8 (c 1.13 in CH$_2$Cl$_2$); v$_{max}$ (film)/cm$^{-1}$ 3215, 2925, 2854, 1667, 1646, 1463, 1427, 1276, 1232, 1171, 1085, 1014, 900, 868, 818, 783, 726 and 715; δ$_H$ (400 MHz, CDCl$_3$) 1.31-1.89 (12H, m, 9× cyclohexyl-H and 8a-CH$_3$), 1.94-2.15 (4H, m, 7-H$_2$ and 8-H$_2$), 2.26 (1H, td, J 13.7 and 4.5, 1× cyclohexyl-H), 3.44-3.51 (1H, m, 3.79-3.86 (1H, m, 6-H$_A$H$_B$) and 6.40 (1H, br s, N—H); δ$_C$ (100 MHz, CDCl$_3$) 19.5 (CH$_2$, 7-C), 20.6 (CH$_2$, cyclohexyl-C), 20.8 (CH$_2$, cyclohexyl-C), 24.5 (CH$_2$, cyclohexyl-C), 25.0 (CH$_3$, 8a-CH$_3$), 33.7 (CH$_2$, cyclohexyl-C), 36.3 (CH$_2$, 8-C), 36.5 (CH$_2$, cyclohexyl-C), 44.7 (CH$_2$, 6-C), 59.5 (quat., 8a-C), 64.0 (quat., 3-C), 168.1 (quat., 4-C) and 171.6 (quat., 1-C); m/z (EI+) 236.15246 (M$^+$. C$_{13}$H$_{20}$N$_2$O$_2$ requires 236.15248).

Example 3

Synthesis of (8aS)-Allyl-hexahydropyrrolo[1,2-a]pyrazine-1,4-dione (Cyclic G-2-AllylP)

Scheme 3: Reagents, conditions and yields:

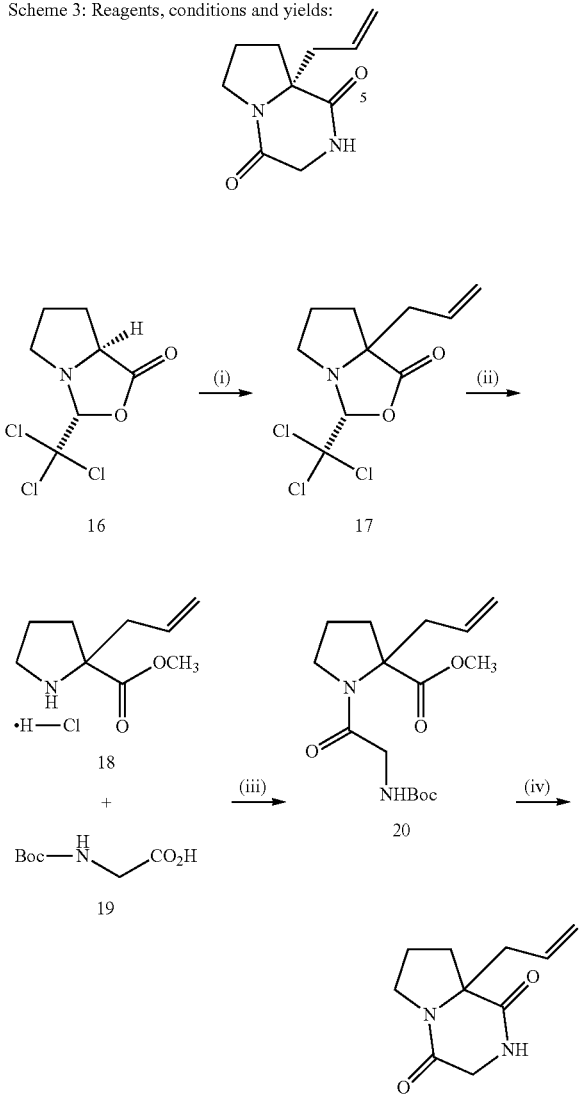

Cyclic G-2AllylP (i) LDA, THF, -78° C., allyl bromide, -78 -> -30° C., N$_2$, 4 h (60%); (ii) acetyl chloride, CH$_3$OH, reflux, N$_2$, 24 h (63%); (iii) Et$_3$N, BoPCl, CH$_2$Cl$_2$, RT, N$_2$, 19.5 h (45%); (iv) TFA, CH$_2$Cl$_2$, 1 h, then Et$_3$N, CH$_2$Cl$_2$, 23 h (37%).

(2R,5S)-4-Allyl-2-trichloromethyl-1-aza-3-oxabicyclo[3.3.0]octan-4-one 17 n-BuLi (1.31M, 9.93 cm$^3$, 13.0 mmol) was added dropwise to a stirred solution of diisopropylamine (1.82 cm$^3$, 13.0 mmol) in dry tetrahydrofuran (20 cm$^3$) at −78° C. under an atmosphere of nitrogen. The solution was stirred for 5 min, warmed to 0° C., stirred for 15 min then added dropwise to a solution of pro-oxazolidinone 16 (2.12 g, 8.68 mmol) in dry tetrahydrofuran (40 cm$^3$) at −78° C. over 20 min and the reaction mixture was stirred for a further 30 min then allyl bromide (2.25 cm$^3$, 26.0 mmol) was added dropwise over 5 min. The solution was warmed slowly to −30° C. over 4 h, quenched with H$_2$O (30 cm$^3$) and the mixture warmed to room temperature and extracted with chloroform (3×80 cm$^3$). The combined organic extracts were dried (MgSO$_4$), filtered and evaporated to dryness in vacuo to produce a dark brown semi-solid which was purified by flash column chromatography (10-20% ethyl acetate-hexane; gradient elution) to produce oxazolidinone 17 (1.48 g, 60%) as an orange oil which solidified at 0° C., for which the nmr data were in agreement with that reported in the literature: $\delta_H$ (400 MHz, CDCl$_3$) 1.58-1.92 (2H, m, Proγ-H$_2$), 1.96-2.14 (2H, m, Proβ-H$_2$), 2.50-2.63 (2H, m, Proδ-H$_2$), 3.12-3.23 (2H, m, CH$_2$—CH=CH$_2$), 4.97 (1H, s, NCH), 5.13-5.18 (2H, m, CH=CH$_2$) and 5.82-5.92 (1H, m, CH=CH$_2$); $\delta_C$ (100 MHz, CDCl$_3$) 25.1 (CH$_2$, Proγ-C), 35.1 (CH$_2$, Proβ-C), 41.5 (CH$_2$, Proδ-C), 58.3 (CH$_2$, CH$_2$CH=CH$_2$), 71.2 (quat., Proα-C), 100.4 (quat., CCl$_3$), 102.3 (CH, NCH), 119.8 (CH$_2$, CH$_2$CH=CH$_2$), 131.9 (CH, CH$_2$CH=CH$_2$) and 176.1 (quat., C=O); m/z (CI+) 284.0009 [(M+H)$^+$. C$_{10}$H$_{13}$$^{35}$Cl$_3$NO$_2$ requires 284.0012], 285.9980 [(M+H)$^+$. C$_{10}$H$_{13}$$^{35}$Cl$_2$$^{37}$ClNO$_2$ requires 285.9982], 287.9951 [(M+H)$^+$. C$_{10}$H$_{13}$$^{35}$Cl$^{37}$Cl$_2$NO$_2$ requires 287.9953] and 289.9932 [(M+H)$^+$. C$_{10}$H$_{13}$$^{37}$Cl$_3$NO$_2$ requires 289.9923].

Methyl L-2-allylprolinate hydrochloride 18

An ice-cooled solution of oxazolidinone 17 (0.64 g, 2.24 mmol) in dry methanol (15 cm$^3$) was treated dropwise with a solution of acetyl chloride (0.36 cm$^3$, 5.0 mmol) in methanol (5 cm$^3$). The solution was heated under reflux for 24 h, then cooled and the solvent removed under reduced pressure. The resultant brown oil was dissolved in toluene (40 cm$^3$) and concentrated to dryness to remove residual thionyl chloride and methanol, then purified by flash column chromatography (5-10% CH$_3$OH—CH$_2$Cl$_2$; gradient elution) to afford hydrochloride 18 (0.29 g, 63%) as a green solid for which the NMR data were in agreement with that reported in the literature: $\delta_H$ (300 MHz, CDCl$_3$) 1.72-2.25 (3H, m, Proβ-H$_A$H$_B$ and Proγ-H$_2$), 2.32-2.52 (1H, m, Proβ-H$_A$H$_B$), 2.72-3.10 (2H, m, Proδ-H$_2$), 3.31-3.78 (2H, m, CH$_2$CH=CH$_2$), 3.84 (3H, s, CO$_2$CH$_3$), 5.20-5.33 (2H, m, CH=CH$_2$), 5.75-5.98 (1H, m, CH=CH$_2$) and 8.06 (1H, br s, N—H); m/z (CI+) 170.1183 [(M+H)$^+$. C$_9$H$_{16}$NO$_2$ requires 170.1181].

Methyl-N-tert-butyloxycarbonyl-glycyl-L-2-allylprolinate 20

Dry triethylamine (0.28 cm$^3$, 2.02 mmol) was added dropwise to a solution of hydrochloride 18 (0.13 g, 0.63 mmol) and N-tert-butyloxycarbonyl-glycine 19 (0.14 g, 0.82 mmol) in dry dichloromethane (35 cm$^3$) under an atmosphere of nitrogen at room temperature, and the reaction mixture was stirred for 10 min. Bis(2-oxo-3-oxazolidinyl)phosphinic chloride (BoPCl, 97%) (0.20 g, 0.80 mmol) was added and the solution stirred for 19.5 h, then washed successively with 10% aqueous hydrochloric acid (35 cm$^3$) and saturated aqueous sodium hydrogen carbonate (35 cm$^3$), dried (MgSO$_4$), filtered and evaporated to dryness in vacuo. Purification of the resultant residue by flash column chromatography (40% ethyl acetate-hexane) yielded dipeptide 20 (0.09 g, 45%) as a light yellow oil: $[\alpha]_D$ +33.8 (c 0.83 in CH$_2$Cl$_2$); $\nu_{max}$ (film)/cm$^{-1}$ 3419, 3075, 2977, 2930, 2874, 1739, 1715, 1656, 1499, 1434, 1392, 1366, 1332, 1268, 1248, 1212, 1168, 1122, 1051, 1026, 1003, 943, 919, 867, 830, 779, 739, 699 and 679; $\delta_H$ (300 MHz, CDCl$_3$) 1.42 [9H, s, C(CH$_3$)$_3$], 1.93-2.08 (4H, m, Proβ-H$_2$ and Proγ-H$_2$), 2.59-2.67 (1H, m, CH$_A$H$_B$CH=CH$_2$), 3.09-3.16 (1H, m, CH$_A$H$_B$CH=CH$_2$), 3.35-3.44 (1H, m, Proδ-H$_A$H$_B$), 3.56-3.62 (1H, m, Proδ-H$_A$H$_B$), 3.70 (3H, s, OCH$_3$), 3.89 (2H, d, J 4.2, Glyα-H$_2$), 5.06-5.11 (2H, m, CH=CH$_2$), 5.42 (1H, br s, Gly-NH) and 5.58-5.72 (1H, m, CH=CH$_2$); $\delta_C$ (75 MHz, CDCl$_3$) 23.7 (CH$_2$, Proγ-C), 28.3 [CH$_3$, C(CH$_3$)$_3$], 35.0 (CH$_2$, Proβ-C), 37.6 (CH$_2$, CH$_2$CH=CH$_2$), 43.3 (CH$_2$, Glyα-C), 47.5 (CH$_2$, Proδ-C), 52.5 (CH$_3$, OCH$_3$), 68.8 (quat., Proα-C), 79.5 [quat., C(CH$_3$)$_3$], 119.4 (CH$_2$, CH=CH$_2$), 132.9 (CH, CH=CH$_2$), 155.7 (quat., NCO$_2$), 166.9 (quat., Gly-CON) and 173.8 (quat., CO$_2$CH$_3$); m/z (EI+) 326.1845 (M$^+$. C$_{16}$H$_{26}$N$_2$O$_5$ requires 326.1842).

(8aS)-Allyl-hexahydropyrrolo[1,2-a]pyrazine-1,4-dione (Cyclic G-2AllylP)

To a solution of dipeptide 20 (0.09 g, 0.28 mmol) in dichloromethane (9 cm$^3$) at room temperature was added trifluoroacetic acid (1 cm$^3$, 0.013 mmol) dropwise and the reaction mixture was stirred for 1 h under an atmosphere of nitrogen. The solution was evaporated under reduced pressure to give a colorless oil which was dissolved in dichloromethane (10 cm$^3$), dry triethylamine (0.096 cm$^3$, 0.69 mmol) was added and the reaction mixture stirred for 4.5 h, after which further triethylamine (0.096 cm$^3$, 0.69 mmol) was added. The reaction mixture was stirred overnight, concentrated to dryness to give a green oil which was purified by flash column chromatography (10% CH$_3$OH—CH$_2$Cl$_2$) to produce cyclic G-2AllylP (20 mg, 37%) as an off-white solid: mp 106-109° C.; $[\alpha]_D$ −102.7 (c 0.95 in CH$_2$Cl$_2$); $\nu_{max}$ (CH$_2$Cl$_2$)/cm$^{-1}$ 3456, 3226, 2920, 1666, 1454, 1325, 1306, 1299, 1210, 1133, 1109, 1028, 1010, 949, 928, 882, 793, 761 and 733; $\delta_H$ (400 MHz, CDCl$_3$) 1.92-2.01 (2H, m, Proγ-H$_2$), 2.09-2.16 (2H, m, Proβ-H$_2$), 2.39-2.56 (2H, m, CH$_2$CH$_2$=CH$_2$), 3.46-3.53 (1H, m, Proδ-H$_A$H$_B$), 3.78-3.87 (2H, m, Proδ-H$_A$H$_B$ and Glyα-H$_A$H$_B$), 4.09 (1H, d, J 17.2, Glyα-H$_A$H$_B$), 5.16-5.20 (2H, m, CH=CH$_2$), 5.73-5.84 (1H, m, CH=CH$_2$) and 7.17 (1H, br s, N—H); $\delta_C$ (100 MHz, CDCl$_3$) 20.1 (CH$_2$, Proγ-C), 34.1 (CH$_2$, Proβ-C), 41.7 (CH$_2$, CH$_2$CH$_2$=CH$_2$), 44.9 (CH$_2$, Proδ-C), 46.4 (CH$_2$, Glyα-C), 67.2 (quat., Proα-C), 120.9

($CH_2$, $CH=CH_2$), 131.0 (CH, $CH=CH_2$), 163.4 (quat., $NCO$) and 171.7 (quat., CONH); m/z (EI+) 195.1132 ($M^+$. $C_{10}H_{15}N_2O_2$ requires 195.1134).

Example 4

Synthesis of (8aS)-Methyl-spiro[cyclopentane-1,3(4H)-tetrahydropyrrolo[1,2-a]pyrazine]-1,4(2H)-dione (Cyclic Cyclopentyl-G-2-MeP)

Scheme 4: Reagents, conditions and yields: (i) $Et_3N$, HOAt, CIP, 1,2-dichloroethane, 83° C., $N_2$, 19 h (23%); (ii) 10% Pd/C, $CH_3OH$, RT, 17 h (65%).

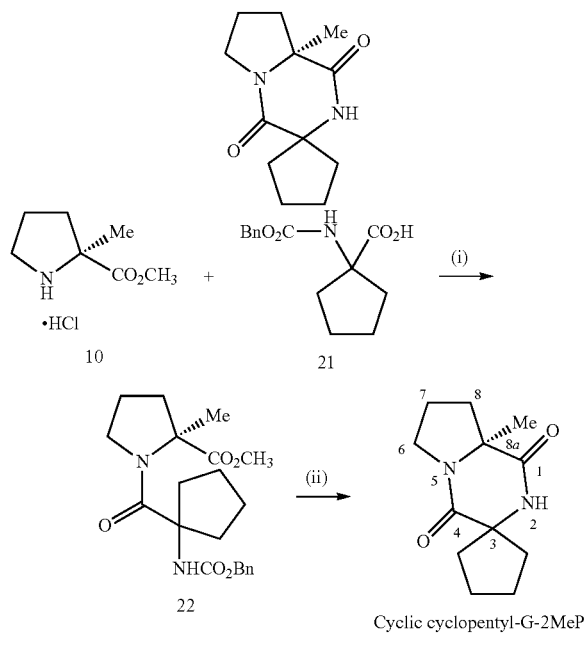

Cyclic cyclopentyl-G-2MeP

N-Benzyloxycarbonyl-1-aminocyclopentane-1-carboxylic acid 21

A solution of benzyl chloroformate (0.290 g, 1.1 mmol) in dioxane (2.5 $cm^3$) was added dropwise to a solution of 1-aminocyclopentanecarboxylic acid (Fluka) (0.2 g, 1.54 mmol) and sodium carbonate (0.490 g, 4.64 mmol) in water (5 $cm^3$) at 0° C. Stirring was continued at room temperature overnight and the reaction mixture washed with ether. The aqueous layer was acidified with 2M hydrochloric acid, extracted with ethyl acetate, dried ($Na_2SO_4$), filtered and the solvent removed to afford carbamate 21 (0.253 g, 62%) as an oil which solidified on standing. Carbamate 21 was shown to be a 70:30 mixture of conformers by $^1$H NMR analysis (the ratio was estimated from the integration of the resonances at $\delta$5.31 and 7.29-7.40, assigned to the N—H protons of the major and minor conformers, respectively): mp 70-80° C. (lit.[1] 82-86° C., ethyl acetate, petroleum ether); $\delta_H$ (400 MHz; $CDCl_3$; $Me_4Si$) 1.83 (4H, br s, 2× cyclopentyl-$H_2$), 2.04 (2H, br s, cyclopentyl-$H_2$), 2.20-2.40 (2H, m, cyclopentyl-$H_2$), 5.13 (2H, br s, $OCH_2Ph$), 5.31 (0.7H, br s, N—H) and 7.29-7.40 (5.3H, m, Ph and N—H*); $\delta_C$ (100 MHz; $CDCl_3$) 24.6 ($CH_2$, cyclopentyl-C), 37.5 ($CH_2$, cyclopentyl-C), 66.0 (quat., cyclopentyl-C), 66.8 ($CH_2$, $OCH_2Ph$), 128.0 (CH, Ph), 128.1 (CH, Ph), 128.4 (CH, Ph), 136.1 (quat, Ph), 155.8 (quat., $NCO_2$) and 179.5 (quat., $CO_2H$).

* denotes resonance assigned to minor conformer.

Methyl N-benzyloxycarbonyl cyclopentyl-glycyl-L-2-methylprolinate 22

Dry triethylamine (0.19 $cm^3$, 1.4 mmol) was added dropwise to a solution of hydrochloride 10 (78 mg, 0.43 mmol), carboxylic acid 21 (0.15 g, 0.56 mmol) and 1-hydroxy-7-azabenzotriazole (Acros) (15 mg, 0.11 mmol) in dry 1,2-dichloroethane (24 $cm^3$) under an atmosphere of nitrogen at room temperature, and the reaction mixture stirred for 10 min. 2-Chloro-1,3-dimethylimidazoliditiium hexafluorophosphate (CIP) (Aldrich) (0.12 g, 0.43 mmol) was added and the resultant solution heated under reflux for 19 h, then washed successively with 10% aqueous hydrochloric acid (30 $cm^3$) and saturated aqueous sodium hydrogen carbonate (30 $cm^3$), dried ($MgSO_4$), filtered and evaporated to dryness in vacuo. Purification of the resultant residue by flash column chromatography (60% ethyl acetate-hexane) yielded amide 22 (39 mg, 23%) as a white solid. Amide 22 was shown to exist as a 3:1 trans:cis mixture of carbamate conformers by $^{13}$C NMR analysis (the ratio was estimated from the relative intensities of the resonances at $\delta$154.1 and 155.7 assigned to the carbamate carbonyl-C atoms of the major and minor conformers, respectively): mp 200-203° C.; $[\alpha]_b$ −54.5 (c 1.52 in $CH_2Cl_2$); $\nu_{max}$ (film)/$cm^{-1}$ 3432, 3239, 3042, 2953, 1736, 1712, 1627, 1540, 1455, 1417, 1439, 1374, 1282, 1256, 1216, 1194, 1171, 1156, 1136, 1100, 1081, 1042, 1020, 107, 953, 917, 876, 756 and 701; $\delta_H$ (400 MHz, $CDCl_3$) 1.33-1.53 (3H, br m, Pro$\alpha$-$CH_3$), 1.62-2.20 (11H, m, Pro$\beta$-$H_2$, Pro$\gamma$-$H_2$ and 7× cyclopentyl-H), 2.59-2.71 (1H, br m, 1× cyclopentyl-H), 3.31-3.42 (1H, br m, Pro$\delta$-$H_AH_B$), 3.58-3.79 (4H, br m, $OCH_3$ and Pro$\delta$-$H_AH_B$), 4.92-5.17 (3H, m, N—H and $OCH_2Ph$) and 7.27-7.42 (5H, s, Ph); $\delta_C$ (100 MHz, $CDCl_3$) 21.7 ($CH_3$, Pro$\alpha$-$CH_3$), 24.1* ($CH_2$, cyclopentyl-C), 24.2 ($CH_2$, cyclopentyl-C), 24.4 ($CH_2$, Pro$\gamma$-C), 24.5 ($CH_2$, cyclopentyl-C), 36.4 ($CH_2$, cyclopentyl-C), 37.1 ($CH_2$, cyclopentyl-C), 37.2* ($CH_2$, cyclopentyl-C), 37.7 ($CH_2$, Pro$\beta$-C), 38.2* ($CH_2$, cyclopentyl-C), 48.5 ($CH_2$, Pro$\delta$-C), 52.1 ($CH_3$, $OCH_3$), 66.6 ($CH_2$, $OCH_2Ph$), 66.9 (quat., Pro$\alpha$-C), 67.2 (quat., Gly$\alpha$-C), 127.8 (CH, Ph), 128.2 (CH, Ph), 128.4 (CH, Ph), 136.6 (quat., Ph), 154.1 (quat., $NCO_2$), 155.7* (quat., $NCO_2$), 170.5 (quat., Gly-CO) and 174.7 (quat., $CO_2CH_3$); m/z (EI+) 388.1991 ($M^+$. $C_{21}H_{28}N_2O_5$ requires 388.1998).

(8aS)-Methyl-spiro[cyclopentane-1,3(4H)-tetrahydropyrrolo[1,2-a]pyrazine]-1,4(2H)-dione (Cyclic cyclopentyl-G-2-MeP)

To a solution of amide 22 (54 mg, 0.14 mmol) in methanol (4.6 $cm^3$) was added 10% Pd on activated charcoal (2.2 mg, 0.021 mmol) and the vessel flushed with hydrogen gas. The resulting suspension was stirred vigorously under an atmosphere of hydrogen for 17 h, then filtered through a Celite™ pad with methanol (15 $cm^3$). The filtrate was concentrated to dryness under reduced pressure to give a yellow semi-solid which was purified by reverse-phase C18 flash column chromatography (0-10% $CH_3CN/H_2O$; gradient elution) to produce cyclic cyclopentyl-G-2MeP (20 mg, 65%) as a yellow solid: mp 160-163° C.; $[\alpha]$©-97.9 (c 1.61 in $CH_2Cl_2$); $\nu_{max}$ (film)/$cm^{-1}$3429, 2956, 2928, 2856, 1667, 1643, 1463, 1432, 1373, 1339, 1254, 1224, 1175, 1086, 1048, 976, 835, 774 and 730; $\delta_H$ (300 MHz, $CDCl_3$) 1.47 (3H, br s, 8a-$CH_3$), 1.56-2.19 (11H, m, 8-$H_2$, 7-$H_2$ and 7× cyclopentyl), 2.58-2.67 (1H, br m, 1× cyclopentyl), 3.48-3.56 (1H, m, 6-$H_AH_B$), 3.72-3.82 (1H, m, 6-$H_AH_B$) and 6.56 (1H, br s, N—H); $\delta_C$ (75 MHz, CDCl$_3$) 19.9 (CH$_2$, 7-C), 24.6 (CH$_2$, cyclopentyl), 24.92 (CH$_3$, 8a-CH$_3$), 24.93 (CH$_2$, cyclopentyl), 36.0 (CH$_2$, 8-C), 38.7 (CH$_2$, cyclopentyl), 41.9 (CH$_2$, cyclopentyl), 44.8 (CH$_2$, 6-C), 64.3 (quat., 8a-C), 66.8 (quat., 3-C), 168.3 (quat., 4-C) and 172.2 (quat., 1-C); m/z (EI+) 222.1369 (M$^+$. C$_{12}$H$_{18}$N$_2$O$_2$ requires 222.1368).

In Vivo Testing

The following pharmacological studies demonstrate efficacy of cyclic G-2AllylP in attenuation of cognitive impairment. They are not intended to be limiting, and other compositions and methods of this invention can be developed without undue experimentation. All of those compositions and methods are considered to be part of this invention. All the following experiments were carried out using protocols developed under guidelines approved by the University of Auckland Animal Ethics Committee.

Efficacy of nootropic drugs can be conveniently tested using models of cholinergic hypofunction. Cholinergic hypofunction has been shown to contribute to dementia-related cognitive decline and remains a target of therapeutic intervention for Alzheimer's disease (Hunter 2004). The cholinergic hypofunction model is also applicable to other conditions. For example, it has been shown that scopolamine-induced cholinergic hypofunction can selectively impair the recognition accuracy of disgust and anger facial expressions rendering the of scopolamine on emotion-recognition similar to those found in Huntington's disease patients (Kamboy 2006). Scopolamine has been commonly used to induce cholinergic hypofunction, and is a well-known model for human Alzheimer's disease, aging and other disorders of cognitive function (Liskowsky et al, Int. J. Dev. Neurosci, 24(2-3):149-156 (2006), Lindner et al., Psychopharmacology (Berl.) Sep. 27 (2006), Bouger et al., Eur. Neuropsychopharmacol 15(3): 331-346 (2005), Ebert et al, Eur. J. Clin. Invest., 28(11):944-949 (1998), Barker et al, Int. J. Geriatr. Psychiatry, 13(4):244-247 (1998), G. Smith, Brain Res. 471(2):103-118 (1998), Flood et al, Behav. Neural. Biol. 45(2):169-184 (1986)).

Example 5

Morris Water Maze (MWM) Model of Learning and Memory Used to Assess Effects of Cyclic G-2-AllylP on Cognitive Function The purpose of the study was to investigate cyclic G-2AllylP in modes of cognitive deficit and affective state (anxiety).

Methods

The first part of the study involved acute testing of the cG-2AllylP in the Morris Water Maze memory model. The MWM test is one of the most frequently used tests for assessing spatial memory in rats and is well recognized to accurately predict effects of disease and treatment on spatial memory generally. Therefore, the MWM test reflects effects of disease and treatment in human subjects.

The standard procedure for MWM was followed. We used a circular swimming pool (80 cm depth×150 cm diameter) filled with opaque water, with the temperature maintained at 20° C. A platform was hidden 1 cm below the water surface, with a white flag (10 cm×10 cm) located either 20 cm above the platform for the visual cue and at 3 o'clock position in relation to the starting location for a spatial cue. On days 1-4 of the experiment rats underwent memory acquisition trials with 6 trials (60 seconds each) in each day of testing (habituation phase). Latency to reach the platform was recorded and the daily reduction of average latency was used to measure the capability to learn where the hidden platform was.

On day 5 of the experiment normal, non-aged Wistar rats were split into groups to receive either saline (n=28) or scopolamine (0.5 mg/kg, i.p., n=27) to induce memory deficit. Scopolamine was administered half an hour before the probe test commenced.

10 min following the scopolamine treatment, the cyclic G-2AllylP was administered orally at 30 mg/kg (n=31) with vehicle-treated animals administered the diluent by oral gavage using an identical treatment protocol (n=24).

Acute effects of cG-2allylP were then tested in animals with scopolamine-induced memory impairment and in age-matched control animals with no memory impairment to determine any direct pharmacological effect on memory processing. Experimental groups are detailed in the Table 1 below.

TABLE 1

Animals Used to Test Effects of cG-2-AllylP on Memory

|  | Scopolamine | Vehicle |
| --- | --- | --- |
| Vehicle | N = 12 | N = 12 |
| cG-2AllylP | N = 15 | N = 16 |

On day 5, the probe MWM test was performed with the platform removed. There were 6 trials, each of maximum duration of 60 s, at least 5 min rest between trials). The amount of time the rats spend swimming near the platform provided a measure of how much they relied on visual and spatial cue to locate the platform, as opposed to using a non-spatial strategy. Data was collected and analysed using Any-maze (v4.2) software.

The data generated from behavioural tests was analysed using one-way ANOVA for determining the difference between the aged-groups. Two-way ANOVA was used for examining the progress of behavioral results with the time points treated as dependent factors. GraphPad Prism version 3.02 was used for data analysis.

Results

Treatment with scopolamine significantly impaired acquisition of spatial memory in treated animals (time to platform approximately 208% of control on day 4). Cyclic G-2AllylP (30 mg/kg; daily) significantly reversed the cognitive impairment induced by scopolamine (FIGS. 1A, 1B, 1C).

Example 6 cG-2-AllylP Improves Synaptic Plasticity and Aging-Related Memory Loss Methods

Aged rats (male Wistar rats, 18-20 months old) were divided into four groups: two vehicle-treated (groups 1 and 3) and two G-2-AllylP treated (groups 2 and 4) (all groups n=6-8). Cyclic G-2-AllylP was synthesised by the Department of Medicinal Chemistry and dissolved in normal saline before the treatment. On day 1a single dose of cyclic G-2-AllylP was given centrally (20 ng/animal, i.c.v.) to the animals in groups 2 and 4; saline was administered to groups 1 and 3. The memory tests using Novel Object Recognition Test started either on day 3 (groups 1 and 2) or 24 (groups 3 and 4) after the treatment. On the completion of the NORT, the rats were killed with an overdose of sodium pentobarbital and were perfused transcardially with normal saline followed by 10% formalin. Tissues collected at day 7 in groups 1 and 2, and at day 28 from groups 3 and 4. The brains were kept in the same fixative for a minimum of 2 days before being processed using a standard paraffin embedding procedure. Briefly, small blocks (10×10×3 mm) of tissue were fixed for up to 24 hrs.

The blocks were then infiltrated and embedded with paraffin and cut in ribbons and mounted on slides. Slides were then stored until immunostaining was commenced. Synaptogenesis in brain tissue was examined using immunohistochemical staining.

Novel Object Recognition Test (NORT)

Exploratory activity is a typical learning behaviour displayed by animals including humans and rats in novel environments. Exploratory activity decreases over time when the novel becomes familiar and the habituation occurs. In familiar environments, exploratory activity can be reactivated by introducing a novel object. The increase in exploring behaviour once the environment is altered following a habituation provides a measure of the memory for the familiarity and the recognition of the novelty.

In this Example, we carried out two NORTs, one at days 3-6 and the other at 24-27 days. The rats were allowed to familiarise themselves with the testing arena (90×60×40 cm) in the first day of NORT. In the following two days of each test, four novel objects were placed into the testing arena and the rats had 2 trials each day (each of 15 min duration and 2 hours apart). The time spent on exploring the objects was reduced once the animal tested learned about the objects (training phase). In the last day (day 4 of each test), one familiar object was replaced by a novel object before the second trial (test 6, testing phase). The average time spent on exploring the 3 familiar objects and the time spent on exploration of the novel object was used as a measure for the memory of familiarity and the novelty recognition.

Effects of cG-2-AllylP on Expression of NMDA Receptors, AMPA Receptors, rKrox-24 and Synaptophysin mRNA in the Hippocampus It is accepted that the hippocampal formations in humans and animals play a crucial role in a number of memory types (Morris et al. 2006 Europ. J. Neurosci. 23, 2829). The specific functionality remains under dispute, but there is an understanding that hippocampus plays a key role in the automatic encoding and initial storage of attended experiences (episodic memory formation), memory consolidation and novelty detection. The first aspect, encoding and short-term storage of memories, is dependant on the synaptic plasticity and synaptic transmission, both of which are linked to glutaminergic neurotransmission.

Glutaminergic transmission is facilitated by two types of glutamate receptors: N-methyl-D-aspartate receptors (NMDAR) and a-amino-3-hydroxy-5-methyl-4-isoxalone propionic acid receptors AMPA or non-NMDA receptors.

APMA receptor subunit GluR1 is a post-synaptic receptor and has been commonly used for memory measurement. GluR1 is believed to mediate calcium influx, and has a vital function in synaptic plasticity related to learning. It has been previously suggested (Hayashi et al., 2000) that incorporation of GluR1 into synapses might be important for long-term potentiation (LTP), which is essential for learning and memory.

It had been demonstrated that NMDA receptor subunit NR1 is crucial for formation of spatial memory. In knock-out models where the R1 subunit of the NMDA receptor in the pyramidal cells of the CA1 region was selectively knocked-out, the long-term potentiation was shown to be abolished (Tsien 1996).

Synaptophysin is a presynaptic vesicle protein. Its quantitative detection is established as a molecular marker of synaptic density.

The neuronal transcript factor Krox24 staining is used as a marker for neuronal plasticity. The protein products of the Krox24 family (as well as by brain-derived neurotrophic factor, BDNF) have recently linked with stabilizing synaptic modifications occurring during NMDA-receptor-mediated hippocampal LTP and LTD. (Dragunow. 2006. Behaviour genetics. 23; 293).

Immunohistochemical Staining

Conventional deparaffinisation and rehydration techniques were used to allow the water-based buffers and antibodies to penetrate the tissue slices. Antigen retrieval was used only prior to AMPA receptor (GluR1) staining, i.e. the slides were placed in boiling citrate buffer and allowed to cool.

The following antibodies were used:
i) primary rabbit antibody to NMDA NR1 subunit, at 1:200 concentration in buffer, incubated for 48 hrs (Chemicon—AB1516), followed by Sigma fluorescent secondary antibody (alexaFluor 594), at 1:200 dilution, incubated for 24 hours at 40 C.
ii) primary antibody to AMPA GluR1 subunit, at 1:50 concentration in buffer, incubated for 48 hrs (Chemicon—AB1504) followed by 3,3'-diaminobenzidine (DAB) at 1:200 dilution, incubated for 24 hours at 40 C.
iii) Primary antibody to mSynaptophysin (Sigma—S5768), at 1:200 concentration in buffer, followed by DAB at 1:200 dilution, incubated for 24 hours at 40 C).
iv) Primary antibody to rKrox-24 (Santa Cruz—catalogue number SC-189) at 1:200 concentration in the buffer, followed by anti-rabbit secondary antibody at concentration of 1:200 dilution, incubated for 24 hours at 40 C.
(e) Antibodies were detected using light microscopy.

Results

NORT

Figure 2:
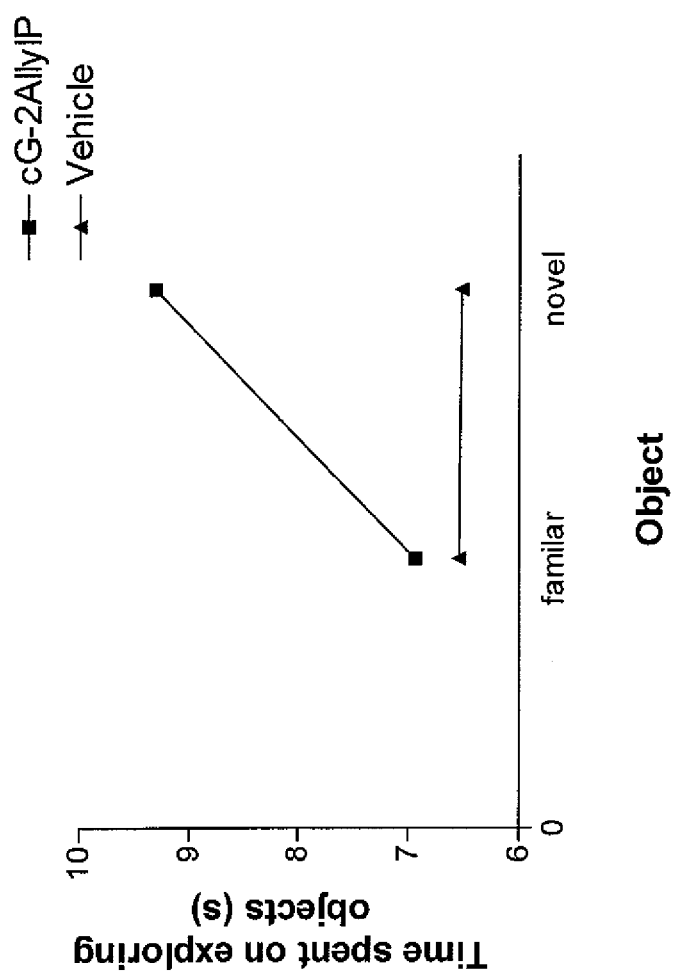
FIG. 2 is a graph showing the difference in time spent on exploring the familiar vs novel object during the probe test on days 25 post-treatment. The data points for familiar objects reflect the average of time spent on exploration of 3 familiar objects. The data point for novel object recognition is the actual time spent exploring the novel object.

A trend to improve the novelty recognition in the groups treated with cG-2AllylP was observed after 27 days (FIG. 2), but not 6 days after the treatment (no figure). We conclude that the cG-2AllyP treatment improved novelty recognition in the drug-treated animals at 27 days.

AMPA Glutamate Receptor-1 Staining

Hippocampal slices from regions CA1 (granular cell layer, strata oriens and radiatum) and CA3 (pyramidal cell layer) were stained for AMPA receptors GluR1.

Figure 4:
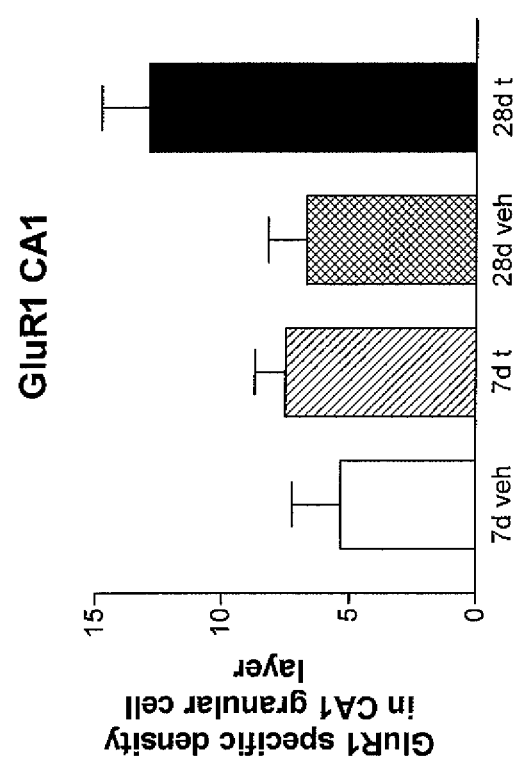
FIG. 4 is a graph showing the effects of cG-2-AllylP (t) on the density of AMPA GluR1 in CA1 granular cell layer on days 6 and 24 in comparison to vehicle (veh).
Figure 5:
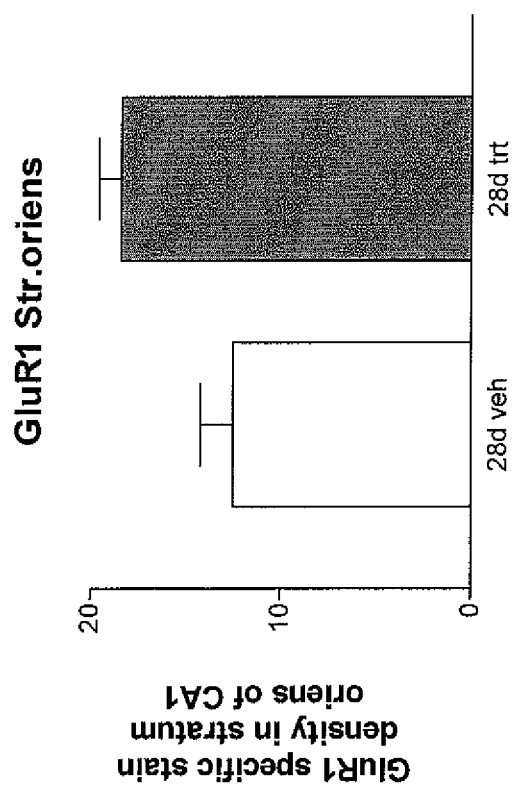
FIG. 5 is a graph showing the effects of cG-2AllylP (t) on the density of AMPA GluR1 in CA1 stratum oriens on day 24 post treatment.
Figure 6:
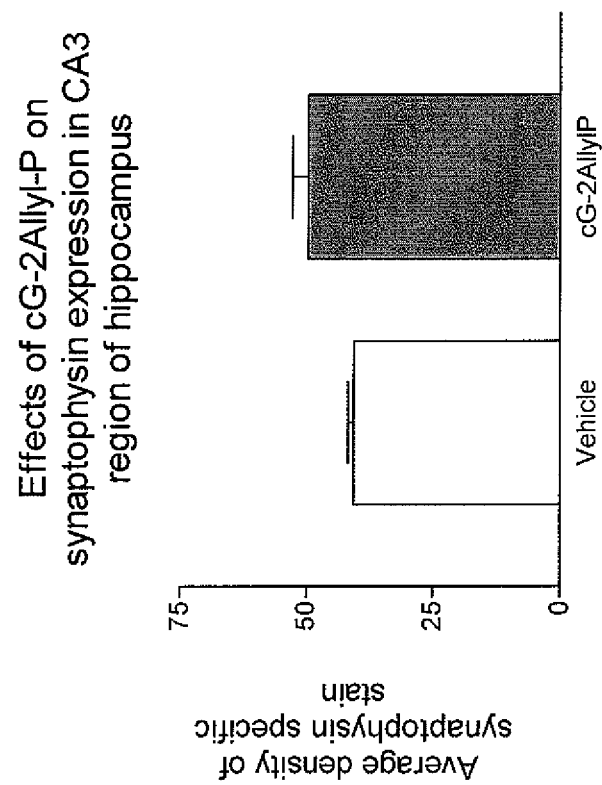
FIG. 6 is a graph showing the effect of cG-2-AllylP on the trend to increase the density of pre-synaptic stain in CA3 region of the hippocampus at day 24 post-treatment.
Figure 7:
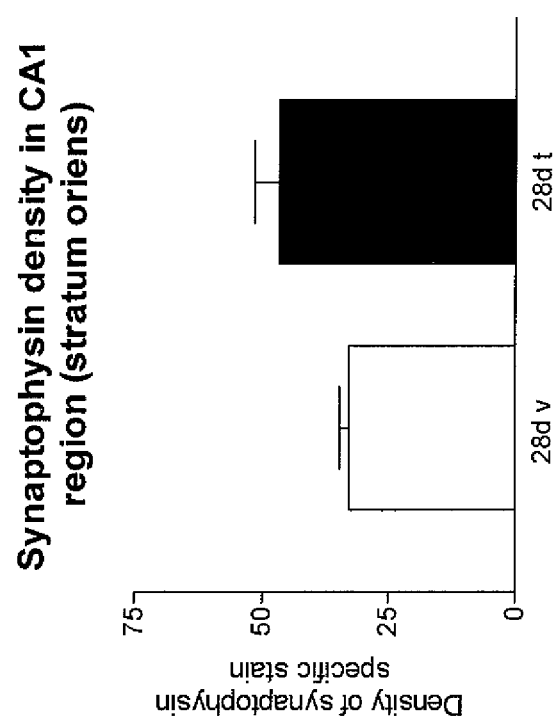
FIG. 7 is a graph showing the effect of cG-2-AllylP on the trend to increase the density of the pre-synaptic stain in the stratum oriens of the CA1 region on day 24 post-treatment.
Figure 8:
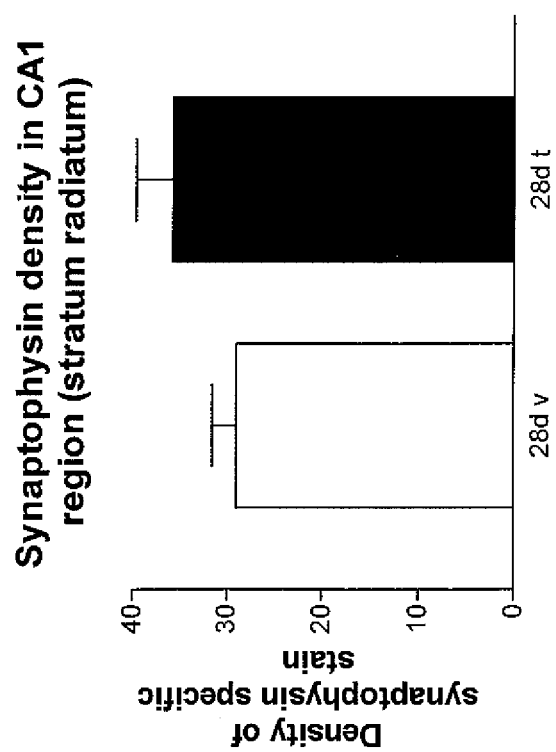
FIG. 8 is a graph showing the effect of cG-2-AllylP to increase the density of the pre-synaptic stain in the stratum radiatum of the CA1 region on day 24 post-treatment FIGS. 9A, B, C are graphs showing the effect of cG-2-AllylP treatment on the density of the NMDAR-1 in CA1 and CA3.

In CA3 there was no change in the number of receptors in each region on either clay 7 or 28. There was however a significant increase in the number of AMPA receptors in CA1 (granular cell layer) (FIG. 4) and CA1 stratum oriens (FIG. 5) and on day 28.

Figure 3:
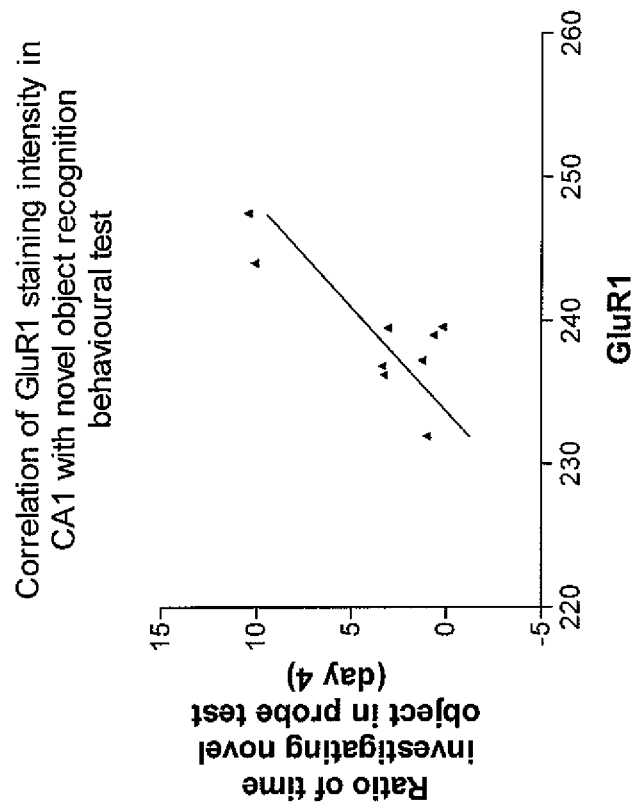
FIG. 3 is a graph showing a correlation between the AMPA glutamate receptor-1 staining of the CA1 region of the hippocampus and the ratio of time spend on investigation of novel object to familiar object in testing phase of the NORT on day 24.

That histological change was correlated with the improved performance in the novel object recognition test. The improved memory (FIG. 2) was correlated to the elevated AMPA glutamate receptor-1 (FIG. 3). We concluded that cG-2AllylP improved glutaminergic neuro-transmission (GluR1) at post-synaptic level.

We observed that cG-2-AllylP treatment resulted in a long term increase in GluR1 staining on the post-synapses and increased the density of pre-synaptic vesicles. As the majority of vesicles in the hippocampus are glutamic vesicles, we concluded that the long term memory improvement was associated with increased glutamic neurotransmission.

Synaptophysin Staining

We subsequently analysed effect of cG-2AllyP on the levels of synaptophysin staining in CA3 and CA1 regions of the hippocampus.

Figures 9A, 9B:
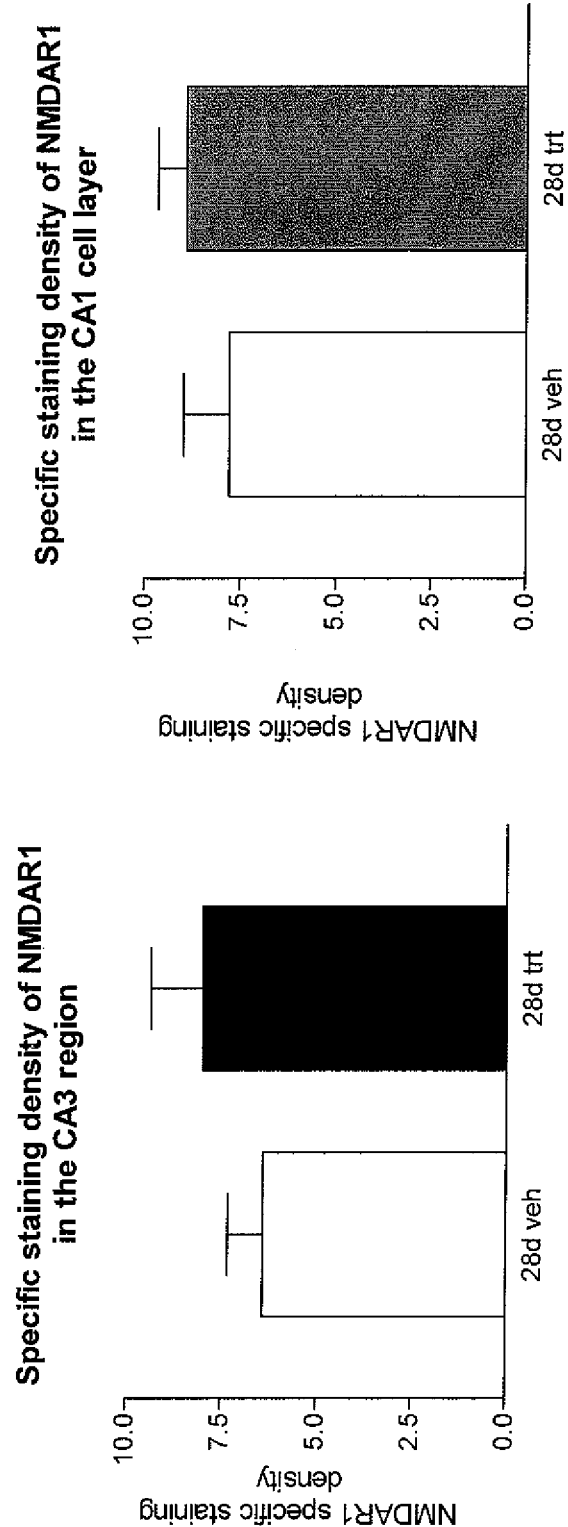
Figure 9C:
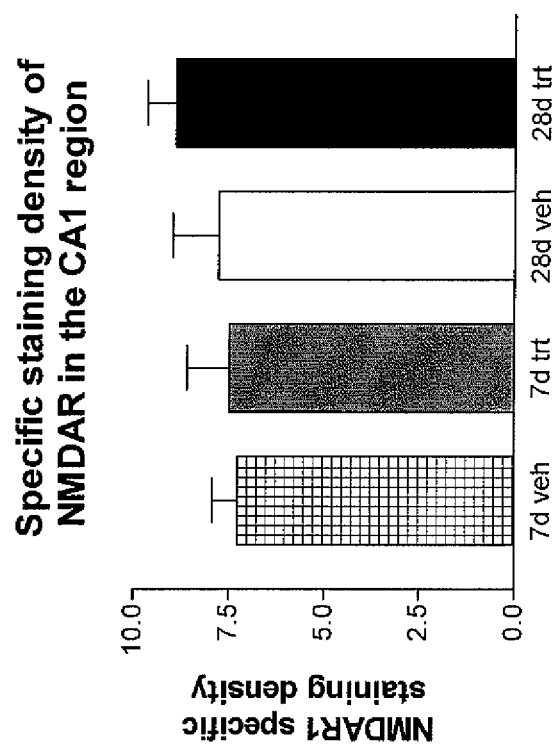
Figure 10:
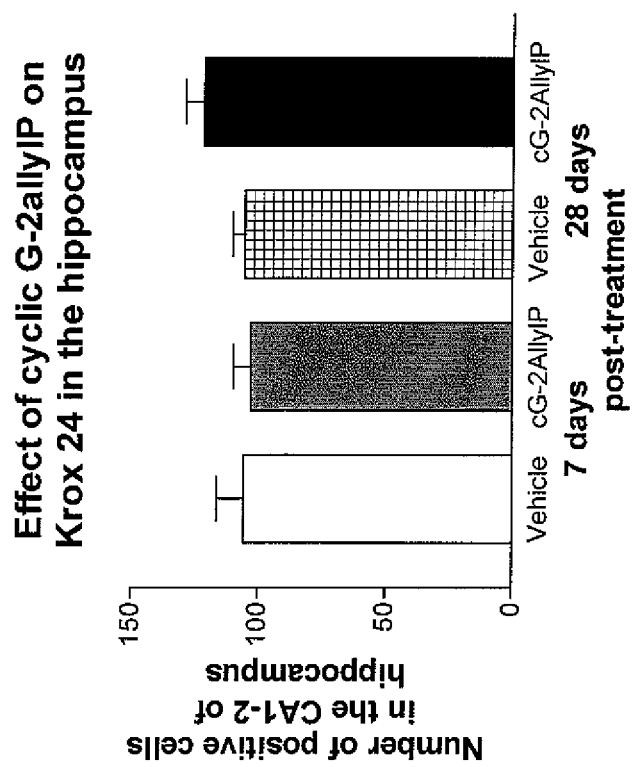
FIG. 10 is a graph showing the effects of cG-2-AllylP on the density of Krox24 staining in the CA 1-2 of the hippocampus.

In all tested areas there was either a significant increase (CA3) or a clear trend towards (CA1—strata oriens and radiatum) the increase in the density of synaptophysin staining at 28 days post-treatment. That increase is a marker of increased synaptic plasticity and a clear indication of synaptogenesis which is a most likely cause of the improvement in the performance of the treated groups in applied memory tests.
NMDA Receptor-1 Staining While there is a significant improvement in AMPA receptors post-treatment, the changes in the NMDA receptors are not so pronounced (FIGS. 9A, 9B and 9C).
Krox24 Staining We analysed the density of the Krox24 staining in the CA 1-2 regions of the hippocampus. We observed a trend towards the increased density in treatment group in comparison to the vehicle treated group. We conclude that the Krox24 staining results positively correlate with improved memory function (FIG. 10).

Example 7 cG-2-AllylP Increases the Number in Pre-Synaptic Vesicles in the Hippocampus of Middle Aged Rats Four middle aged Wistar male rats (12 months) were divided into two groups: one vehicle-treated (n=2) and one cG-2-AllylP-treated (n=2). The rats were treated subcutaneously with 3 mg/kg/day of either saline or cG-2-AllylP for 7 days. On day 21 of the experiment the animals were sacrificed and the hippocampal tissue was harvested. Semi-thin sections of the tissue were fixed with $OsO_4$ and embedded in resin. CA1 stratum oriens and CA3 sections were then sliced into ultra-thin, 80 nm slices and stained with uranyl acetate and lead citrate. Approximately 50 synapses per animal were analysed, synapse type classified and vesicle density was measured using AnalySIS®.

Figure 11:
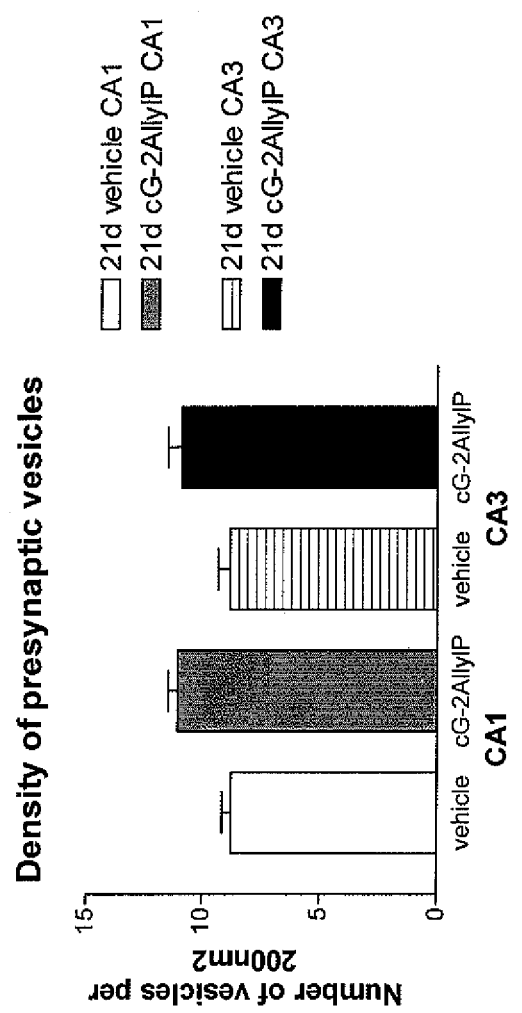
FIG. 11 is a graph showing the effects of cG-2-AllylP on the number of vehicles in a 200 nm² square apposing the post-synaptic density in subregions CA3 and CA1 of the hippocampus of middle aged rats (n=2 in each group).

Transmission electron microscopy was used to count the total number of vesicles on the slides. The average density was calculated by measuring the total area (using AxioVision software) and using the number of vesicles. We followed the protocol in Yoshida et al. 97, Journal of Neurochemistry to calculate the vesicle density in a 200 nm×200 nm square apposing the post-synaptic density (PSD).
Results The number of pre-synaptic vesicles in the CA1 and C3 subregions of the hippocampus was increased after cG-2-AllylP treatment (3 mg/kg/day×7 days, s.c.) compared to the vehicle treated animals at 21 days after the treatment (FIG. 11).

We conclude from these studies that scopolamine treatment can decrease cognitive function in animals, and that these changes can mimic cognitive impairment in human beings with one or more of a variety of neurological conditions. Additionally, we conclude that cG-2-AllylP can improve cognitive function in scopolamine-treated animals and in animals with normal aging-related cognitive impairment. Further, we conclude that cG-2-AllylP can increase synaptogenesis, increase AMPA receptors, increase neural plasticity, can stabilize synaptic modifications and can increase novelty recognition.

These studies therefore support the use of eG-2-AllylP as an effective pharmacological agent to treat a variety of cognitive impairments in animals including humans suffering from Alzheimer's disease, Parkinson's disease, and other chronic neural disorders, as well as cognitive impairment associated with aging.
In Vitro and In Vivo Testing The following pharmacological studies demonstrate neuroprotective features of this invention. They are not intended to be limiting, and other compositions and methods of this invention can be developed without undue experimentation.

All of those compositions and methods are considered to be part of this invention. All the following experiments were carried out using protocols developed under guidelines approved by the University of Auckland Animal Ethics Committee.

Example 8

Effects of Cyclic G-2-AllylP and Cyclic cyclopentyl-G-2MeP on Cerebellar Cell Explants To determine the effects of cG-2-AllylP and cyclic cyclopentyl-G-2-MeP on neuronal cells in vitro, a series of studies was carried out using cerebellar explants from adult rats. In vitro systems are suitable for studying neuronal proliferation, neurite growth, formation of nerve bundles, and effects of toxins on neural cells, effects that parallel effects observed in vivo. Thus, results of studies using in vitro cerebellar explants are predictive of effects of interventions in vivo.

In a first series of studies, effects of glutamate on cerebellar explants were determined. At physiological concentrations, glutamate is a neurotransmitter in the CNS of mammals, including humans. However, at sufficiently high concentrations, glutamate is neurotoxic, resulting in neuronal cell death. Because glutamate is a naturally occurring neurotransmitter in the CNS of mammals, including humans, and because glutamate neurotoxicity is recognized in the art as reflective of neurotoxicity in general, and including cell death and degeneration, it is a valuable tool useful for identifying and characterizing agents effective in treatment of neurodegeneration and neural cell death.
Materials and Methods Cover slips were placed into a large Petri dish and washed in 70% alcohol for 5 minutes, then washed with Millipore $H_2O$. The cover slips were air dried, and coated with Poly-D-Lysine (1 mg/ml stock solution in PBS, 90-100 µl) for 2 hours at 34° C.
Extraction of Cerebellar Tissue Postnatal day 8 Wistar rats were used for the study. The rats were sacrificed and placed in ice for 1 minute, decapitated and the cerebellum removed and placed on ice. Cerebellum tissue was placed in 1 ml of 0.65% glucose-supplemented PBS (10 µl 65% stock D (+)glucose/1 ml PBS) in a large Petri dish, chopped up into smaller sections and triturated with a 1 ml insulin syringe via a 23 G (0.4 mm) needle, and then squirted back into the glucose solution in the large Petri dish. The tissue was sieved through (125 µm pore size gauze) and centrifuged (2 minutes at 60 g) twice to exchange the medium into serum-free BSA-supplemented START V medium (Biochrom, Germany). The second centrifugation step was done with 1 ml of START V medium. The microexplants were reconstituted into 500 µl of START V medium and put on ice.
Cultivation of Cerebellar Cells Two hours after PDL-coating, the slides were washed with Millipore $H_2O$ and air dried. Each slide was placed into a small Petri dish (diameter: 35 mm) and 40 µl of START V/cell suspension was added. The tissue was incubated for 2 hours at 34° C. (settlement period). START V-medium (1 ml) was then added to the Petri dish and cultivated at 34° C. in the presence of 5% $CO_2$ in air at 100% humidity for 48 hours.
Drug Application For the study, certain explant cultures were exposed to vehicle (PBS) only. In the first study (Study 1) 10 µl of toxin 1 (L-glutamate-100 mM in Millipore water; final concentration: 1 mM) and 10 µl of toxin 2 (3-nitropropionic acid—50 mM—pH 7—in Millipore water, final concentration: 0.5 mM) was applied simultaneously with the drug to be tested (10 mM stock solution prepared in PBS and diluted to final concentrations between 1-100 nM). In each case, the drugs were left in contact with the explants for the duration of the study.

Methods for Determining Drug Effects

After explants were exposed to drugs for the study period, cells were then rinsed in PBS and then fixed in increasing concentrations of paraformaldehyde (500 μl of 0.4% PFA was applied; then 1.2% PFA; then 3% PFA and finally 4% PFA (each fixation step: 2-3 minutes). Finally, the microexplants were rinsed in PBS.

Neurons in the explants were then evaluated for morphology (presence of neurites) and counted as live cells per microscopic field. Four fields displaying highest cell density were counted per cover slip and the data presented as mean±standard error of the mean (SEM); n=4 each. Statistical significance was evaluated by using the non-paired Student's t-test.

Results

Cyclic G-2-AllylP

Figure 12:
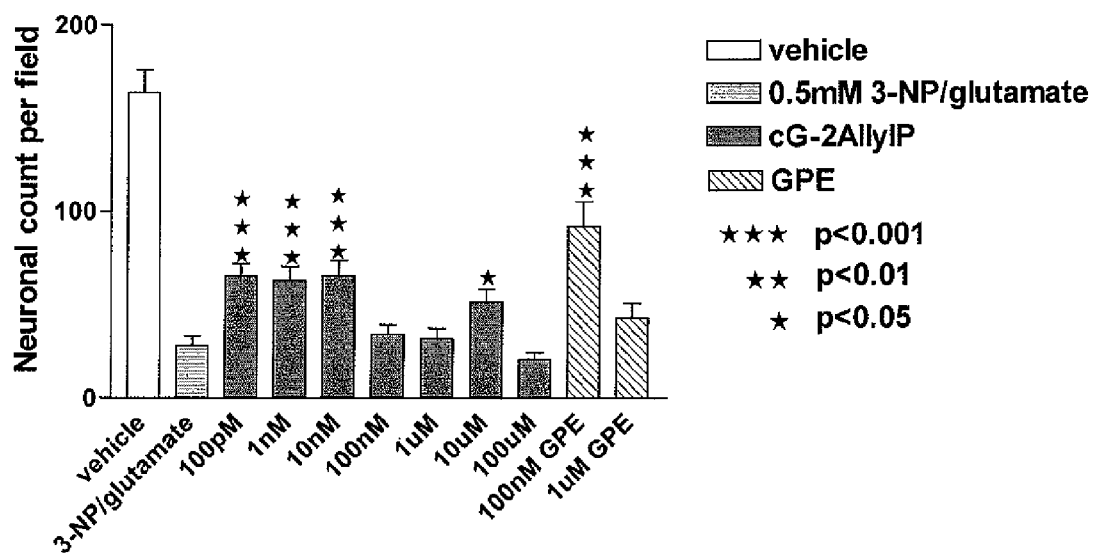
FIG. 12 is a graph showing effects of cyclic G-2-AllylP on neuronal survival in animals following excitotoxic oxidative stress.

The results of the study are shown in FIG. 12. Glutamate treatment (1 mM; filled bar) resulted in about an 85% loss of cerebellar neurons having neurites compared to vehicle-treated controls (open bar). In contrast, cG-2AllylP significantly increased the numbers of cells having neurites in a dose-dependent manner when administered simultaneously with glutamate (shaded bars). Treatment with low doses of cG-2AllylP (100 pm to 10 nm) showed a significant decrease in glutamate-induced neurotoxicity.

Cyclic cyclopentyl-G-2-MeP

Figure 13:
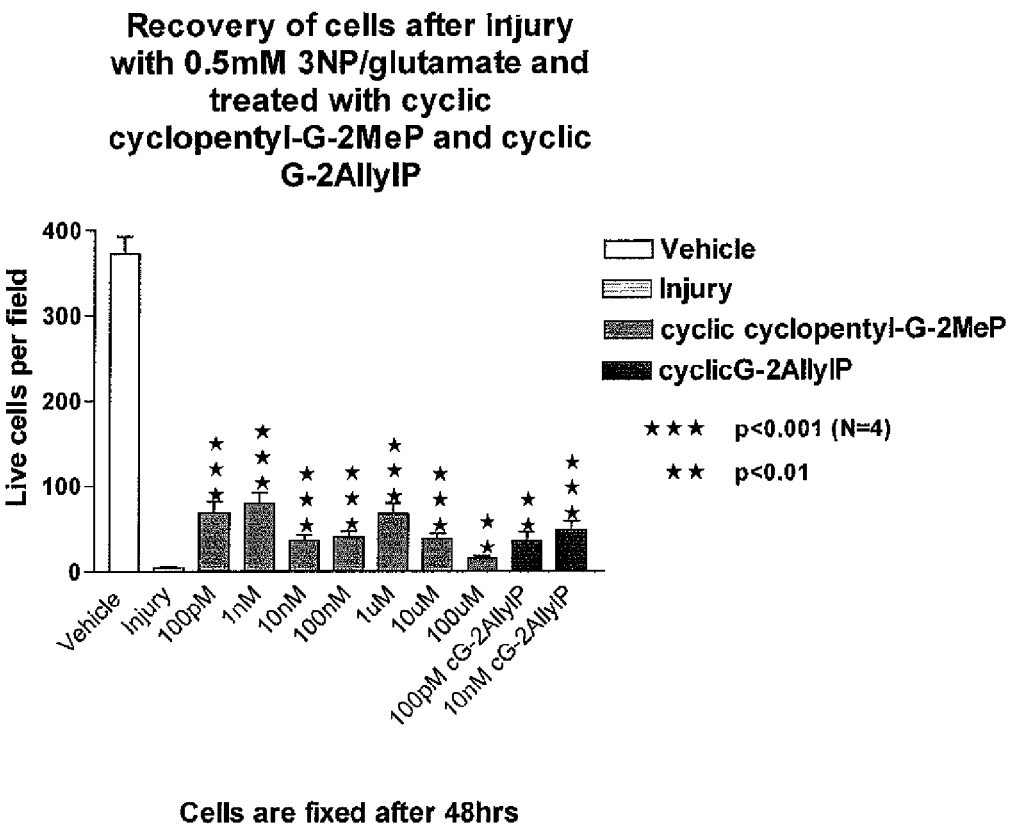
FIG. 13 is a graph showing effects of cyclic cyclopentylG-2-MeP on neuronal survival in animals following excitotoxic oxidative stress.

The results of the study are shown in FIG. 13. Cyclic cyclopentyl-G-2MeP significantly increased the number of cells having neurites when simultaneously administered with glutamate (light shaded bars). Treatment with low doses of cyclic cyclopentyl-G-2MeP showed a significant decrease in glutamate-induced neurotoxicity.

Conclusions

Both cG-2-AllylP and cyclic cyclopentyl-G-2-MeP independently decreased or prevented glutamate-induced neurotoxicity, indicating that both drugs are neuroprotective and can be used to inhibit neuronal degeneration or cell death.

Example 9

Effects of cG-2-AllylP on Hypoxic-Ischemic Injury I

Materials and Methods

To determine whether cG-2AllylP might prevent neuronal injury in response to stroke, cardiac arterial bypass graft surgery (CABG) or other hypoxic insults, a series of studies were carried out in rats that had been exposed to hypoxic-ischemic injury (HI). Adult rats (Wistar, 280-310 g, male) were used. The modified Levine model preparation and experimental procedures were used (Rice et al, 1981, *Ann. Neurol.*: 9: 131-141; Guan et al J., 1993, *Cereb. Blood Flow Metab.*: 13(4): 609-16). These procedures in brief, consist of an HI injury induced by unilateral carotid artery ligation followed by inhalational asphyxia in the animals with an implanted lateral ventricular cannula. A guide cannula was stereotaxically placed on the top of the dura 1.5 mm to the right of the mid-line and 7.5 mm anterior to the interaural zero plane under halothane anaesthesia. The right carotid artery was double ligated two days after the cannulation. After 1 hour recovery from the anaesthesia, each of the rats were placed in an incubator where the humidity (90±5%) and temperature (31°±0.5° C.) were controlled for another hour, then exposed to hypoxia (6% oxygen) for 10 min. The animals were kept in the incubator for an additional 2 hours before treatment.

Nine pairs of rats were treated intracerebral ventricularly (icv) with either cG-2AllylP (2 ng) or its vehicle (normal saline) 2 hours after hypoxic-ischemic insult. Rats in each group were simultaneously infused with cG-2-AllylP or its vehicle under light anaesthesia (1.5% halothane) 2 hours after the insult. A total volume of 20 μl was infused (icv) over 20 minutes by a micro-infusion pump.

Histological examination was performed on rats 5 days after the hypoxic-ischemic injury. The rats were killed with an overdose of sodium pentobarbital and were perfused transcardially with normal saline followed by 10% formalin. The brains were kept in the same fixative for a minimum of 2 days before being processed using a standard paraffin imbedding procedure.

Coronal sections 8 μm in thickness were cut from the striatum, cerebral cortex and hippocampus and were stained with thionin and acid fuchsin. The histological outcome was assessed at three levels: (1) the mid level of the striatum, (2) where the completed hippocampus first appeared and (3) the level where the ventral horn of the hippocampus just appears. The severity of tissue damage was scored in the striatum, cortex and the CA1-2, CA3, CA4 and dentate gyrus of the hippocampus. Tissue damage was identified as neuronal loss (acidophilic (red) cytoplasm and contracted nuclei), pan-necrosis and cellular reactions. Tissue damage was scored using the following scoring system: 0: tissue showed no tissue damage, 1: <5% tissue was damaged, 2: <50% tissue was damaged, 3: >50% tissue was damaged and 4: >95% tissue was damaged.

Results and Conclusion

Figure 14:
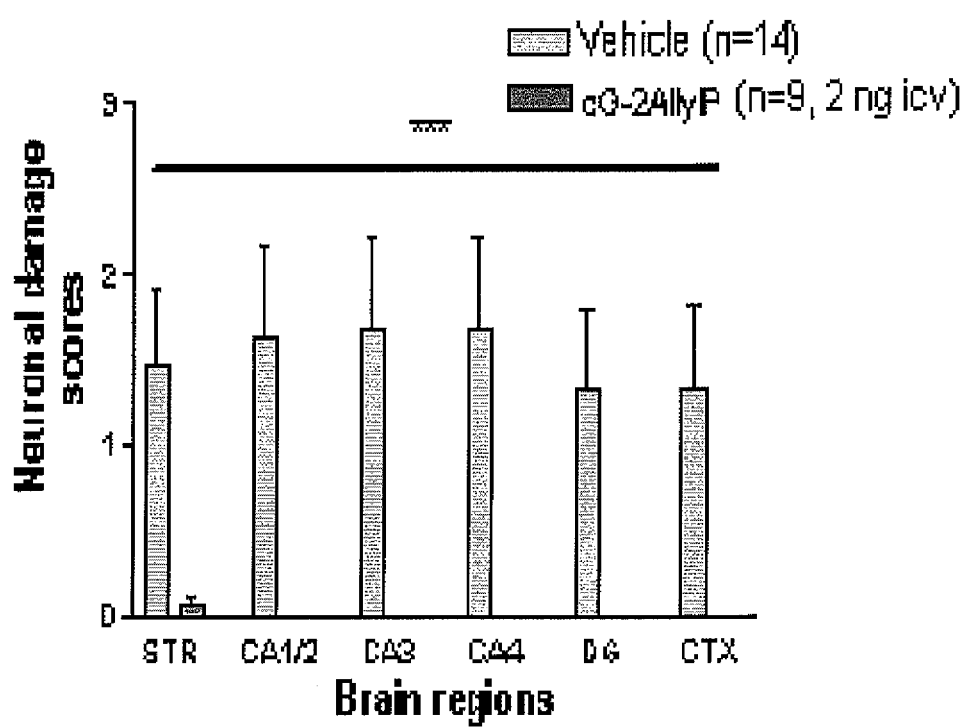
FIG. 14 is a graph showing the neuroprotective effects of cyclic G-2-AllylP in animals subjected to global brain ischaemia.

The results of this study are shown in FIG. 14. FIG. 14 shows that hypoxic-ischemic injury (left bars of each set) resulted in significant damage scores in each of the areas of the brain studied. FIG. 14 also shows that central administration of a relatively low dose of cG-2-AllylP (right bars of each set; 2 ng) significantly reduced the tissue damage in each brain region examined compared to the vehicle treated group ($p < 0.001$).

It can be seen that cG-2-AllylP can be neuroprotective against neural damage caused by hypoxic-ischemic injury, even when administered after hypoxic-ischemic injury. This surprising finding indicates that cG-2-AllyP is a useful agent to treat a variety of conditions characterized by neural degeneration or cell death.

Example 10

Effects of cG-2-AllylP on Hypoxic-Ischemic Injury II Materials and Methods

Materials and methods described in Example 9 were used and the number of treatment groups was increased. Rats were divided into 5 treatment groups treated intracerebral ventricularly (icy) with one of 4 doses of cG-2-AllylP or with its vehicle (normal saline) 2 hours after hypoxic-ischemic insult (1: n=10, 2 ng; 2: n=9, 4 ng; 3: n=9, 20 ng; 4: n=10, 100 ng; and 5: n=9, vehicle).

Figure 15:
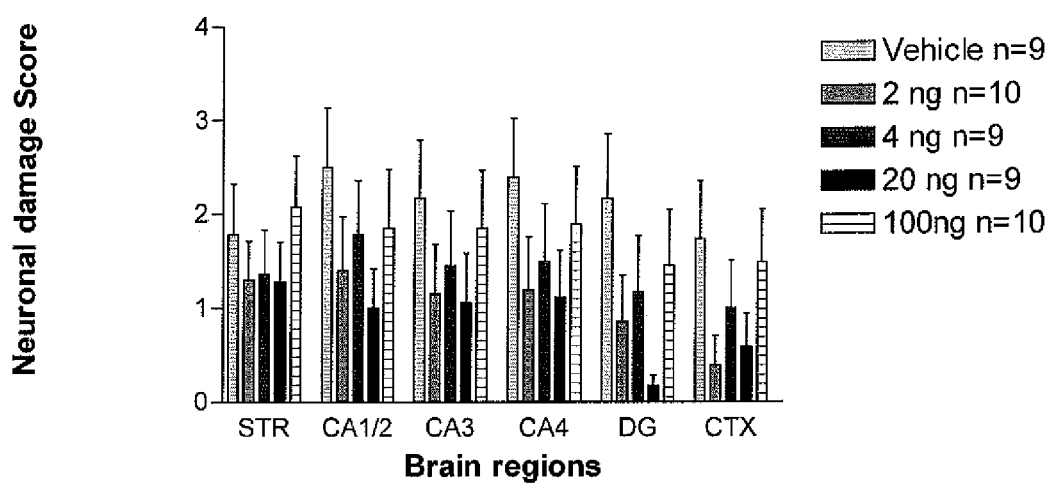
FIG. 15 is a graph showing effects of different doses of cyclic G-2-AllylP on neuroprotection in animals subjected to global brain ischaemia.

FIG. 15 shows hypoxia alone (vehicle) produces neuronal damage scores in all areas of the brain studied. In animals treated with cG-2-AllylP, hypoxia had less effect, even though the agent was administered after the hypoxic/ischemic injury. The neuroprotective effect was observed for all doses of cG-2-AllylP, except for the highest dose (100 ng) administered to the striatum. However, in all other sites and with all other doses, cG-2-AllylP lessened the neural damage effects of hypoxia/ischemia. Moreover, cG-2-AllylP had an increased efficacy in brain regions that experienced progressive injury associated with delayed cell death, such as that associated with apoptosis. In brain regions such as the dentate gyrus and the cerebral cortex, that are more resistant to HI injury, the progression of injury is known to be slower and more severe than in the brain regions that are more sensitive to HI injury such as the striatum and the CA1-2, CA3 and CA4 sub-regions of the hippocampus. This result shows that cG-2allylP can be beneficial in treatment of chronic neurological disorders.

This invention is described with reference to specific embodiments thereof. Other features and embodiments of this invention can be produced by those of skill in the art without undue experimentation and a reasonably likelihood of success. All of those embodiments are considered to be part of this invention.

What is claimed is:

1. A method for relieving or alleviating of cognitive impairment caused by a disease, injury, or condition in a mammal in need thereof, comprising: administering a pharmaceutically effective amount of cyclic Glycyl-2-Allyl Proline (cG-2-AllyIP) to said mammal, where said disease is selected from the group consisting of Alzheimer's disease, Huntington's disease, Lewy Body disease, Dementia, and multi-infarct dementia, said injury is selected from the group consisting of neurotoxic injury, cerebral hypoxia/ischemia, traumatic brain injury, coronary artery bypass surgery, where said condition is normal aging, age-related memory loss, memory impairment, cholinergic hypofunction, vascular narrowing or blockage in the brain, neuroinflammation, mild cognitive impairment, cerebral atrophy, frontotemporal lobar degeneration, Pick's disease, HIV infection, Down's syndrome, and loss of synaptic plasticity.

2. The method of claim 1, wherein said cG-2-AllyIP comprises an aqueous solution and one or more pharmaceutically acceptable excipients, additives, carriers or adjuvants.

3. The method of claim 1, wherein said cG-2-AllylP further comprises one or more excipients, carriers, additives, adjuvants or binders in a tablet or capsule.

4. The method of claim 1, wherein said disorder is a mild cognitive impairment or a dementia.

5. The method of claim 1, wherein said cyclic G-2-AllyIP is administered via an oral, intraperitoneal, intravascular, peripheral circulation, subcutaneous, intraorbital, ophthalmic, intraspinal, intracisternal, topical, infusion, implant, aerosol, inhalation, scarification, intracapsular, intramuscular, intranasal, buccal, transdermal, pulmonary, rectal, or vaginal route.

6. The method of claim 1, wherein said effective amount has a lower limit of about 0.001 milligrams per kilogram mass (mg/kg) of the animal and an upper limit of about 100 mg/kg.

7. The method of claim 1, wherein said cognitive impairment is caused by cholinergic hypofunction.

8. The method of claim 1, wherein said cognitive impairment is age-related memory loss.

9. The method of claim 7, wherein said cholinergic hypofunction is caused by scopalamine.

10. The method of claim 1, wherein said cognitive impairment is caused by a decrease in glutamate receptors in the granular cell layer (CA1) of the hippocampus of said mammal.

11. The method of claim 1, wherein said cG-2-AllylP causes an increase in AMPA receptors in the granular cell layer (CA1) of the hippocampus of said mammal.

12. The method of claim 1, wherein said cG-2-AllylP causes an increase in neuronal plasticity caused by said cG-2-AllylP in the granule cell layer (CA1) and the pyramidal cell layer (CA3) regions of said mammal's hippocampus.

13. The method of claim 1, wherein said cG-2-AllylP causes an increase in spatial memory in said mammal.

14. The method of claim 1, wherein said cG-2-AllylP causes in increase in novelty recognition in said mammal.

15. The method of claim 1, wherein said cG-2-AllylP improves glutaminergic neurotransmission in the hippocampus of said mammal.

16. The method of claim 1, wherein said cG-2-AllylP causes an increase in the number of pre-synaptic vesicles in the CA1 and C3 regions of said mammal's hippocampus.

17. The method of claim 1, wherein said cG-2-AllylP causes an increase in synaptic density in the hippocampus of said mammal.

18. The method of claim 1, said cerebral hypoxia/ischemia caused by traumatic brain injury.

19. The method of claim 1, said cognitive impairment caused by multi-infarct dementia.

20. The method of claim 1, said cognitive impairment caused by coronary arterial bypass surgery (CABG).

21. The method of claim 1, said cognitive impairment caused by decreased cerebral perfusion.

22. The method of claim 1, said cognitive impairment caused by normal aging.

* * * * *